(12) United States Patent
Bagamery et al.

(10) Patent No.: US 11,364,001 B2
(45) Date of Patent: Jun. 21, 2022

(54) IMAGING DEVICE AND TOMOGRAPHY APPARATUS COMPRISING THE IMAGING DEVICE

(71) Applicant: MEDISO Medical Imaging Systems Kft., Budapest (HU)

(72) Inventors: Istvan Bagamery, Budapest (HU); Tamas Bukki, Szendehely (HU); Andras Wirth, Budapest (HU)

(73) Assignee: Mediso Medical Imaging Systems KFT., Budapest (HU)

( * ) Notice: Subject to any disclaimer, the term of this patent is extended or adjusted under 35 U.S.C. 154(b) by 716 days.

(21) Appl. No.: 15/689,179

(22) Filed: Aug. 29, 2017

(65) Prior Publication Data
US 2018/0103918 A1 Apr. 19, 2018

(30) Foreign Application Priority Data
Oct. 14, 2016 (HU) .................................. P1600577

(51) Int. Cl.
*A61B 6/06* (2006.01)
*G21K 1/02* (2006.01)
(Continued)

(52) U.S. Cl.
CPC ................ *A61B 6/06* (2013.01); *A61B 6/037* (2013.01); *G01T 1/1648* (2013.01); *G21K 1/02* (2013.01); *G21K 1/025* (2013.01); *G01T 1/1642* (2013.01)

(58) Field of Classification Search
CPC .............................................. G01N 2021/8636
See application file for complete search history.

(56) References Cited

U.S. PATENT DOCUMENTS

2004/0232348 A1 11/2004 Beckman
2004/0262525 A1 12/2004 Yunker et al.
(Continued)

FOREIGN PATENT DOCUMENTS

WO 2014033489 8/2012

OTHER PUBLICATIONS

Hungarian Intellectual Property Office, Search Report for corresponding HU P1600577.

*Primary Examiner* — David P Porta
*Assistant Examiner* — Carolyn Fin
(74) *Attorney, Agent, or Firm* — Wood Herron & Evans LLP

(57) ABSTRACT

The invention is an imaging device comprising detector and collimator element (144) applied e.g. in a SPECT. In the imaging device according to the invention the collimator element comprises—one or more first pinholes (146a, 148a) being focussed on a central field of view (141), the one or more first pinholes (146a, 148a) being adapted for projecting the central field of view (141) on one or more respective first imaging regions (52) being non-overlapping with any other imaging regions;—one or more second pinholes (148b) being focussed on a central field of view (141), the one or more second pinholes (148b) being adapted for projecting the central field of view (141) on one or more respective second imaging regions (56);—one or more second pinholes (148c) being focussed on a primary field of view (142) comprising the central field of view (141), the one or more third pinholes (148c) being adapted for projecting the primary field of view (142) on one or more respective third imaging regions (58) overlapping with at least one second imaging region (56). The invention is furthermore a tomographic apparatus (e.g. a SPECT) comprising the imaging device. (FIG. 13).

14 Claims, 16 Drawing Sheets

(51) Int. Cl.
*A61B 6/03* (2006.01)
*G01T 1/164* (2006.01)

(56) References Cited

U.S. PATENT DOCUMENTS

| | | |
|---|---|---|
| 2008/0087829 A1 | 4/2008 | Hoppin et al. |
| 2015/0115161 A1* | 4/2015 | Bagamery ............... G06F 30/00 250/361 R |

* cited by examiner

IMAGING DEVICE AND TOMOGRAPHY APPARATUS COMPRISING THE IMAGING DEVICE

TECHNICAL FIELD

The invention relates to an imaging device comprising a detector and a collimator element, and to a tomography apparatus (e.g. SPECT apparatus) comprising the imaging device.

BACKGROUND ART

SPECT (single-photon emission computed tomography) apparatuses capable of performing in vivo scans of various organisms constitute an important diagnostic tool for nuclear medicine, medical imaging. In SPECT imaging the molecules taking part in biological processes (e.g. metabolism) are marked applying radioisotopes emitting gamma photons, i.e. a gamma-emitting isotope is bonded by radiochemical methods to a molecule that takes part in a biological, for example metabolic process. The objective of the imaging process is to accurately (quantitatively) determine the distribution of the isotope, and thereby to characterize the biological functioning of the organ(s) under examination.

Most of the time, a planar gamma detector or detectors are applied for the measurements. When multiple detectors are applied, these are arranged around the object/patient to be examined. The detector/detectors may be stationary or may be rotated around the object to be examined, acquiring recordings of the object to be examined from different sides in order to increase the amount of independently measured information. Based on the signals acquired from the position-sensitive gamma detector (capable of determining the incidence location of gamma photons) the location of the interaction between the gamma photon and the material can be determined (with a given level of uncertainty).

A collimator is a device adapted for letting through to the detector only those photons that arrive from specific directions. To achieve that, a single pinhole (so-called pinhole arrangement) or multiple pinholes (so-called multi-pinhole arrangement) can be applied. Having obtained the interaction location on the detector (the incidence location of the gamma photon), based on the model of the collimator the region of the object under examination at which the gamma photon originated can be determined. Based on the measured information and the imaging model of the collimator the isotope distribution inside the object/organ being examined can be calculated; this process is termed "image reconstruction". The accuracy of the reconstructed image is determined among others by the activity administered to the patient, the specific accumulation/binding of the activity and the measurement duration. The quality of imaging and the closely related contrast to noise ratio (CNR, see K. Vunckx, D. Beque, M. Defrise, and J. Nuyts, Single and multipinhole collimator design evaluation method for small animal SPECT, *IEEE Trans. Med. Imag.*, vol. 27, no. 1, pp. 36-46, January 2008.) fundamentally depends on the number of the applied views (i.e. the number of independent measurements), as well as on the imaging characteristics of the imaging system, e.g. the gamma sensitivity and the intrinsic resolution of the detector (the resolution determined by the construction of the detector). The parameters of the imaging system are also highly dependent on the configuration of the collimator that is adapted for imaging the object, and also on the relative spatial position of the collimator, the detector, and the object to be imaged.

In pinhole imaging such a collimator device is applied that lets gamma radiation only through a small-size hole (having a typical diameter of 0.2-6 mm), and thus generates an image of the object under examination on the detector by means of a camera obscura-like projection. The term "detector" is taken to refer collectively to a scintillation crystal typically setting up the detector, of which the incidence plane is called the incidence surface, to light-sensitive photodetectors (typically photomultiplier tubes [PMT] or silicon photomultiplier tubes [SiPMT]) adapted for detecting scintillations of the scintillation crystal, and to the electronics adapted for processing the electric signals of the photodetectors. The scintillation crystal and the photodetectors connected thereto may be replaced by other gamma detectors, by way of example ionization chambers or even gamma-sensitive solid-state detectors, such as position-sensitive CZT (cadmium zinc telluride) detectors.

The sensitivity of the imaging can be significantly increased by arranging a plurality of pinholes in the collimator, i.e. by applying a multi-pinhole (abbreviated hereinafter as MP) imaging. The pinholes are physically located in a collimator element of a collimator. The collimator has typically a truncated pyramidal shape, with the base of the pyramid being constituted by the detector. The pinholes are formed in a collimator element arranged parallel with the detector (accordingly the collimator element may also be termed "aperture" or "aperture element"). The lateral surfaces (mantle) of the truncated pyramid are adapted for preventing scattered radiation from reaching the detector from lateral directions, i.e. they ensure that (gamma) photons can only arrive to the detector through the collimator element. The distance of the detector and the collimator element is of course kept fixed during the imaging process.

The collimator element (aperture) is therefore the part of the collimator which comprises the pinholes. The collimator element is typically configured in two ways:

1. The collimator element is a plate-shaped element with bores formed in it. Inserts defining the shape of the pinhole can be placed in the bores. This configuration allows that the plate of the collimator element and the inserts can be made of different materials.

2. Alternatively, the pinholes can also be formed in the plate-shaped collimator element itself, for example by means of electrical discharge machining.

In both cases the collimator element may be made of a different material than other parts (typically, the lateral surfaces of the truncated pyramid) of the collimator. Option 1 above is advantageous because it allows that only the spatial region around the pinholes—rather than the entire collimator—is made of a material with special properties (for example, high density). The collimator element therefore forms a part of the collimator (it is integrated in the collimator element), and is typically implemented as a high-density (flat) block (made e.g. of Tungsten) or a curved-surface body, e.g. a cylindrical ring. Therefore, a flat collimator element is typically applied together with a truncated pyramidal collimator; while a cylindrical collimator element is typically surrounded by the detector elements.

The individual pinholes provide projections on partially or fully different regions of the detector. The projections can be non-overlapping (see e.g. FIG. 1, and also the U.S. Pat. No. 7,145,153 B2 and U.S. Pat. No. 9,261,608 B2), in which case the projections provided by the different pinholes lie at different regions of the detector surface, or the projections may comprise overlaps (see by way of example U.S. Pat.

No. 7,199,371 B2), in which case parts of the projected images lie at the same regions of the detector, i.e. they overlap with each other.

Applying overlapping MP projections can significantly improve the sensitivity of imaging (essentially, the average sensitivity calculated for the unit-size reconstructible field of view (generally abbreviated as FOV)), but at the same time, depending on activity distribution and on the kind of the overlaps on the detector between the projections may introduce a significant amount of artifacts, i.e. may cause falsely reconstructed activity distribution in the reconstructed image (see e.g. K. Vunckx et al., Effect of Overlapping Projections on Reconstruction Image Quality in Multipinhole SPECT, IEEE Trans. Med. Img. vol. 27, no. 7, (2008)).

As it was mentioned above, in some cases overlapping projection scheme is applied. For example, applying the NanoSPECT pre-clinical SPECT apparatus it has been shown (see U.S. Pat. No. 7,199,371 B2) that in MP imaging no considerable (significant) amount of artifacts is introduced provided that the activity distribution is fundamentally inhomogeneous, such as in the case with active nodules or metastases appearing in oncology examinations. At the same time, in brain or cardiology examinations the activity distribution is extensive, since in the former case in addition to the striatum a significant activity is exhibited also by the white matter and the cortical region, while in the latter case in addition to the heart and the cardiac muscles also the liver and intestinal contents have considerable activity. Therefore, a considerable amount of activity can be found outside the region under direct investigation.

The artifacts introduced by the overlaps appear in the reconstructed image space because the spatial regions containing activity are imaged by the collimator element in an ambiguous manner (i.e. they are imaged inconsistently), i.e. an activity-comprising spatial region is projected on such a detector element on which another spatial region is also projected. In case of a non-overlapping projection scheme activity is projected on a given detector element from multiple different voxels arranged along a straight line, the inconsistency introduced this way is resolved in an unambiguous manner by other views obtained, for example, by rotating the detector about the object under examination.

In such cases the reconstruction algorithm is typically unable to determine unambiguously the pinhole through which the given signal is measured, therefore it calculates a contribution for more than one spatial regions, which may finally result in a false activity distribution. With iterative reconstruction schemes based on EM (Expectation Maximization) or OSEM (Ordered Subset Expectation Maximization) the inconsistency induced by overlapping projections results in that the given spatial region converges slower to the real activity (in the reconstructed volume the convergence rate is significantly reduced in the overlapping regions) and thus the artifacts appearing in the image space disappear slower (or converge to a false fixed point). Since (due to noise accumulation) the reconstruction is typically halted at a given number of iteration steps, with an inconsistent projection scheme typically considerable artifact remains in the image space.

Artifact-free constructions applying overlapping projections are disclosed in a study by A J. Lin, IEEE Trans. Med. Img. On Artifact-Free Projection Overlaps in Multi-Pinhole Tomographic Imaging, vol. 32, no. 12, (2013). Among others, such an imaging construction is disclosed wherein in transaxial view (a view perpendicular to the axis of rotation of the SPECT apparatus) the entire field of view (FOV) is projected on a given region of the detector in a non-overlapping manner, with mutually overlapping projections being also made of the same section. The non-overlapping projection is applied for filtering out artifacts, i.e. the inconsistency of overlapping projections is resolved by that the FOV is imaged by certain pinholes and the projections corresponding thereto in a complete and artifact-free manner. The non-overlapping, consistent projections hold an amount of information by themselves that is sufficient for reconstructing the FOV in an artifact-free manner. It is confirmed also by this study that the commonly held view on overlapping projections produced on the detector surface is that they typically result in the appearance of artifacts.

In U.S. Pat. No. 9,168,014 B2 a concept of the central field of view appears, defined such that it corresponds to the intersection of the respective fields of view of the pinholes. This central field of view is therefore imaged by each of the pinholes. The approach according to the document may further comprise such pinholes that are adapted for imaging the volume situated around the central field of view. The figures of the document show non-overlapping imaging on the detector surface in all cases.

In EP 2 482 101 B1 an approach applying overlapping projections is disclosed wherein the difficulties introduced by overlaps are solved by a dedicated physical device, a so-called pinhole shutter device that is adapted for opening and closing the pinholes independent of one another and thus for eliminating the overlap on the detector by keeping simultaneously open only such pinholes which provide non-overlapping projections on the detector. The data of these image recordings—that are disadvantageously recorded non-simultaneously—are combined in the reconstruction algorithm. A further disadvantage of such multiple-stage imaging is that only one third/half of the pinholes are open simultaneously at a time, so the effective sensitivity of the imaging is reduced to half or to one-third.

In the study by K. Van Audenhaege et al., The Evaluation of Data Completeness and Image Quality in Multiplexing Multi-Pinhole SPECT, IEEE Trans. Med. Img. vol. 34, no. 2, (2015) a method (a so-called "de-multiplexing" method) is disclosed for resolving the inconsistency (in the wording of the study, the "multiplexing") introduced by the overlaps produced on the detector that provides for artifact-free imaging making use of a rotating detector. In this case the spatial region to be examined is imaged by another pinhole proportionally to the imaging provided by the pinhole applied in the first position. In the method described in the study it is supposed that the conditions for ideal pinhole projection are fulfilled (i.e. the hole is pointlike and has a configuration free from gamma penetration).

In EP 2 360 494 A2 such a central field of view or focal volume (according to the terminology of the document) is defined that lies at the intersection of the projections of the pinholes formed in the collimator element encompassing the central field of view, i.e. this focal volume can be "seen" by all of the pinholes belonging to a given group of pinholes. It is possible to define more than one such focal volumes; such pinholes can be assigned each focal volume, by means of that the given focal volume can be projected. According to the figures of the document, non-overlapping projections correspond to the pinholes. In EP 2 360 494 A2 a single field of view is defined and is termed the central field of view based on the characteristic that it is situated at the intersection region of the projections provided by the pinholes. A similar arrangement is disclosed in U.S. Pat. No. 8,067,741 B2.

Further pinhole imaging arrangements are disclosed in US 2013/0161520 A1, U.S. Pat. No. 8,653,464 B2 and US 2011/0158384 A1.

In the light of the known approaches a need has arisen for an imaging device by means of which bodily organs situated in delimited regions can be examined as effectively and artifact-free manner as possible.

DESCRIPTION OF THE INVENTION

The primary object of the invention is to provide an imaging device and a corresponding tomography apparatus which are free from disadvantages of prior art approaches to the greatest possible extent.

A further object of the invention is to provide an imaging device by means of which a larger field of view as well as the organs situated in delimited regions inside it can be examined as effectively as possible. An object of the invention is to provide an imaging device by means of which a body and, in addition to that, also of an organ of said body (situated by way of example inside a larger field of view containing the entire body) can be reconstructed artifact-free as completely as possible.

The objects according to the invention can be achieved by the imaging device according to claim 1 and a tomography apparatus according to claim 10. Preferred embodiments of the invention are defined in the dependent claims.

According to the invention, therefore, inside an arbitrary field of view (designated generally with the acronym FOV) a highlighted (emphasized, prominent) field of view (CFOV, central field of view) preferably comprising an organ accumulating an activity density that is higher than the activity density of the background is imaged with as favourable imaging characteristics as possible. These better imaging characteristics are achieved by arranging non-overlapping and overlapping imaging regions on the detector according to the invention. Thus, according to the invention, some of the imaging regions are required not to overlap with others, while an overlap is explicitly required between other imaging regions. Therefore, according to the invention, by an appropriate arrangement (combination) of overlapping and non-overlapping projections, it is provided in case of imaging a given field of view that a central portion thereof (which preferably comprises a high-activity organ) is imaged with particularly favourable imaging characteristics.

The imaging device according to the invention and the tomography apparatus according to the invention comprising the imaging device allow for recording an image of a spatial region with arbitrary activity distribution such that a highlighted spatial region (central field of view) is imaged with particularly favourable imaging characteristics, while such an imaging of the activity situated around the highlighted region is also provided that has as good imaging characteristics as possible.

In the present description the field of view (commonly abbreviated as FOV) comprising (encompassing, involving) the central field of view (CFOV) is termed a primary field of view (based on its location it may also be termed a main, encompassing or external field of view, or it may be called a principal or entire field of view). Alternatively, the primary and the central field of view could simply be termed a first and a second field of view; what is important is that the second field of view is situated (arranged) inside the first field of view. In the following, the primary and central field of view (central FOV) are also termed the primary FOV and the CFOV. The primary and central field of view can also be called the primary space of view and the central space of view, respectively.

In the present invention, therefore—unlike in certain known approaches—the CFOV is determined by the location of the targeted organ to be examined (the organ has to fall into the CFOV), for which the collimator element is configured (the projections of the collimator element indicate the extent to which the CFOV and the primary FOV encompassing it is "viewed", i.e. projected).

According to the invention, special MP projection schemes (pinhole arrangements and orientations) and, closely related to that, special detector segmentation solutions are presented, which, compared to conventional solutions provide significantly higher CNR, i.e. reduced background noise with higher contrast, in the CFOV region. This is achieved by a special, partially overlapping (i.e. overlapping for a part of the projections) imaging which is adapted for unambiguously imaging activity inside the CFOV, and also images the entire primary FOV. Thereby it becomes possible to eventually reconstruct the CFOV in an artifact-free manner (because activity in the portion of the primary FOV situated outside the CFOV can also be reconstructed). In addition to that, the imaging device and tomography apparatus according to the invention also significantly reduces the occurrence of artifacts resulting from overlaps in the regions outside the CFOV since—as it is illustrated in FIG. 4—certain regions are made consistent also in the primary FOV in spite of the overlapping projection. In addition to the imaging device, the invention also relates a tomography apparatus, preferably a SPECT apparatus comprising the imaging device.

In case the dimensions of the applied gamma detector are significantly larger than the dimensions of the organ to be examined, it is worth considering the possibility of MP imaging. Such a situation may occur e.g. when a SPECT camera adapted for human whole-body imaging is desired to be utilized for organ-specific imaging (i.e. for imaging a much smaller subregion instead of the whole body), for example for heart, kidney, or brain examinations. For example, in a brain examination with a Parkinson's disease indication the region of interest is constituted by certain nuclei (i.e. the striatum) situated in the inner region of the brain. In such a case preferably an imaging focussing on the given organ, that is, in this case on the striatum situated in the middle region of the brain has to be provided because thereby the important imaging parameters, e.g. sensitivity, resolution, CNR of the given region can be improved significantly, and thus the diagnostic value of the examination can also be improved. In order to achieve an imaging with appropriate imaging characteristics it is important that the given pinhole is focussed on the target region, i.e. that the projection is substantially directed to that region. If focussing was not provided at all or was insufficient, i.e. the projection would cover a much wider region (of which the target region is only a small section), then satisfactory imaging characteristics could not be attained.

At the same time, activity situated in a given spatial region can only be reconstructed with sufficient accuracy and without artifacts if in the given transaxial plane (in the section perpendicular to the axis of rotation applied in SPECT imaging) there is no significant activity present outside the FOV to be imaged.

For example, in scans utilizing DaTscan (which is a Parkinson's disease-specific material comprising $^{123}$I, developed for the visualization of dopamine transport), in addition to the striatum a considerable amount of $^{123}$I activity is taken up by the cortical region and the white matter, which activity is frequently utilized as a reference by the physician. Thus, for providing an artifact-free and quantitatively accurate imaging of the striatum situated deep inside the brain the entire brain has to be imaged, because otherwise activity present outside the striatum may alter (even significantly) the results obtained in the reconstruction. In this case therefore the primary FOV has to be defined such that (to a good approximation) it comprises (encompasses) the entire brain.

In such cases a target region that comprises the organ or group of organs that is the object of (i.e. it is of interest for) the examination (investigation), i.e. the central field of view (CFOV) introduced above can be defined. The collimator element of the imaging system is intended to be designed such that it can image the CFOV region with as favourable imaging characteristics as possible. At the same time, with the collimator element it is also possible to acquire a sufficient amount of information from the region surrounding the CFOV that comprises a considerable amount of activity (in spite of the fact that the "target organ", i.e. the organ of the highest interest is located in the CFOV), that is, the regions inside the primary FOV (the primary FOV encompasses the CFOV) such that the region inside the CFOV can be reconstructed in an artifact-free manner. In the present application the primary FOV is taken to comprise (encompass, involve, include) the CFOV and also the region around the CFOV. That is, the entire field of view is termed the FOV, with the CFOV being a part of it. Besides that, such an approach could also be applied according to which only the region surrounding the CFOV is termed the primary FOV; in this case therefore the primary FOV and the CFOV would be separated (disjunct) spatial regions.

Such an imaging scheme can be termed "multi-region imaging" because instead of defining a single region (field of view, FOV) for the imaging as is generally done, but the region is divided into two parts: a highlighted region (CFOV) and another region surrounding (and comprising) the CFOV which also carries valuable information (the primary FOV). The amount of artifacts present in the CFOV can be significantly reduced (or the artifacts can even be eliminated) in case the given region of the image space is unambiguously imaged by another detector or detector segment, thereby resolving the inconsistency of projection.

BRIEF DESCRIPTION OF THE DRAWINGS

Preferred embodiments of the invention are described below by way of example with reference to the following drawings, where.

MODES FOR CARRYING OUT THE INVENTION

In the following a multiple-region MP projection scheme (with a centrally situated CFOV being defined inside the primary FOV, thereby defining both the former highlighted region and the preferably lower-activity region surrounding it) realising specially arranged overlaps on the detector (on the surface thereof) is presented that allows for reconstructing the CFOV (comprising the organ with significant activity) in an artifact-free manner as completely as possible.

In the following the imaging device according to the invention is presented schematically with a flat collimator element and a flat detector incidence surface, in transaxial view (a section perpendicular to the axis of rotation of the SPECT apparatus and, thus, to the field of view axis of the FOV), emphasising the key points of its operation. The invention can also be carried out applying, for example, a curved collimator element. The principles set forth in relation to the invention can also be applied/generalised for such a collimator element and detector.

Figure 1:
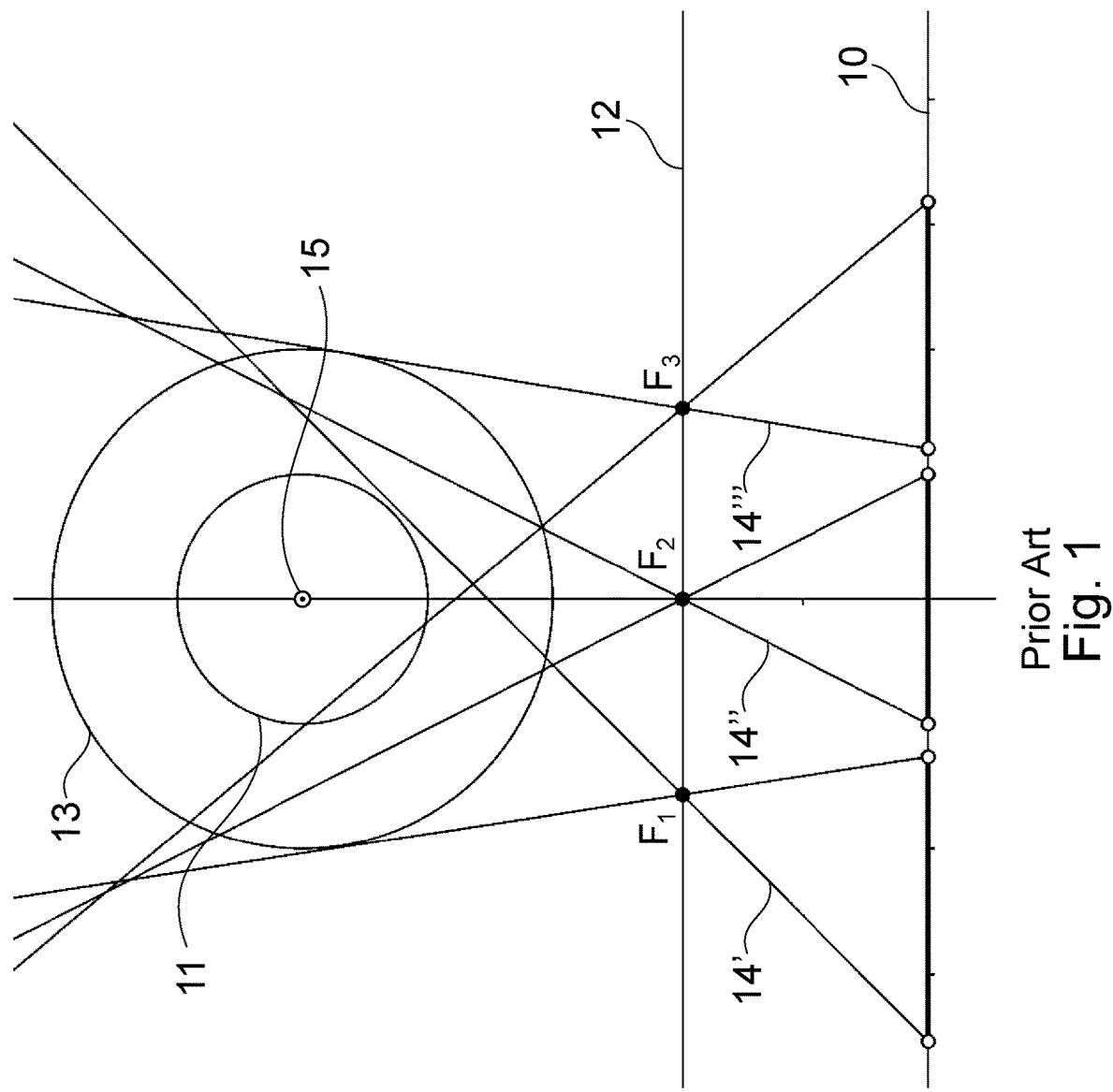
FIG. 1 illustrates an imaging according to a prior art approach in a so-called transaxial view (i.e. a section perpendicular to the axis of rotation of the SPECT apparatus)

Let us first consider an MP imaging in FIG. 1 illustrated in transaxial view, wherein three focal points ($F_1$, $F_2$, $F_3$) are defined. In this example the three focal points are situated in a common focal plane 12, and the projection is non-overlapping. In FIG. 1 a detector 10 is shown, and projections 14', 14", 14''' arriving onto the detector 10 through pinholes formed at the focal points $F_1$, $F_2$, $F_3$ are also shown. In FIG. 1 a transaxial view of a central field of view 11 (CFOV) is shown (a circular region), with a view of a primary field of view 13 comprising the central field of view 11 (the view of the primary field of view also has a circular boundary line being concentric with the CFOV view).

In the transaxial view illustrated in FIG. 1, the projection 14" projects the entirety of the central field of view 11, with the lines indicating the boundaries of the projection 14"

running outside the central field of view 11, at a certain distance from the boundary of the central field of view 11. Accordingly, the projection 14'' also images a significant part of the primary field of view 13 situated outside the central field of view 11. The projection 14' is targeted at the primary field of view 13, with the boundary of the projection extending along the boundary of the primary field of view 13 in a transaxial view, and with its other extremity going across the primary field of view 13; according to the transaxial view of the figure, the central field of view 11 is projected by the projection 14'. The projection 14''' is arranged similarly to the projection 14' but in the transaxial view shown in the figure it is directed (focussed) to the other extremity of the primary field of view 13, and only images a major part of the central field of view 11. As shown in FIG. 1, the three projections 14', 14'', 14''' collectively image the entire primary field of view 13—in the given transaxial view—that is, by way of these projections 14', 14'', 14''' unambiguous projection information is obtained of all portions of the primary field of view 13 (since the projections 14', 14'', 14''' are laid out in a non-overlapping manner on the detector 10).

The applied projections typically cover the detector in an optimal way (i.e. the incidence surface thereof used for imaging purposes), that is, the available useful (sensitive) surface of the detector (UFOV—useful field of view) is tiled perfectly by the projections in a regular or irregular square or hexagonal grid.

According to the above, the pinholes are formed in the collimator element. The pinholes formed either in insert elements made of high-density material (typically Tungsten, but the material may be other high-density metal or alloy, or a composite material, by way of example the mixture of powdered Tungsten and a binder material) or in the collimator element itself, preferably having a pyramidal configuration (cf. FIG. 13, in which the configuration of the pinholes is shown in sectional view; from the small-sized pinholes a respective truncated pyramid-shape opens towards the field of view and towards the detector). The adjustment of the extent of projection overlap on the detector or a non-overlapping projection can be provided in itself by the configuration of the pinholes (the distance of the detector and the collimator element is of course an important factor since the quality of the tiling (the rate of coverage) and the extent of the overlaps are affected by this parameter, and accordingly it is imperative that the detector and the collimator element are situated at a fixed distance from each other), i.e. there is no need to apply supplementary screening in the invention.

In the collimator element of the imaging device according to the invention the bore of the pinholes preferably follows the shape of the projections, so in case of a rectangular projection (i.e. a projection with a rectangular projected image on the detector) the pinholes have rectangular cross-section; while in case of a conical projection they have circular or elliptical cross-section. However, the shape of the bores need not necessarily correspond to the shape of the projection. The shape of the projection can be determined solely by the inlet and outlet apertures of the pinholes (by way of example, a pinhole can have an expanding shape but a relatively narrower outlet aperture negates its effect; cf. also the loft-hole approach: WO 2011/070123 A2). From the aspect of manufacturing technology the application of rectangular cross-section bores may be advantageous.

Bores with rectangular cross sections also have rectangular inlet and outlet apertures, and accordingly the corresponding projections on the detector are also rectangular. Rectangular projections are advantageous also for the tiling of the detector (for controlling the amount of overlaps).

In order that the organs situated in the CFOV can be imaged with the best possible imaging characteristics, the focal plane or more generally, focal surface situated in the collimator element has to be placed as close as possible to the FOV to be imaged (and thus, also to the CFOV). Besides that, it is expedient to adjust as many pinholes as possible such that they can image the CFOV as completely as possible (even in its entirety). (The extent to which this objective is fulfilled is illustrated by transaxial and axial views in the following examples, where the structure of the projections provided by the imaging device according to the invention is presented in some embodiments.) A portion of the pinholes are applied for imaging the region situated outside the CFOV but inside the FOV in order that the part lying inside the CFOV can be reconstructed in an artifact-free manner.

Figure 2:
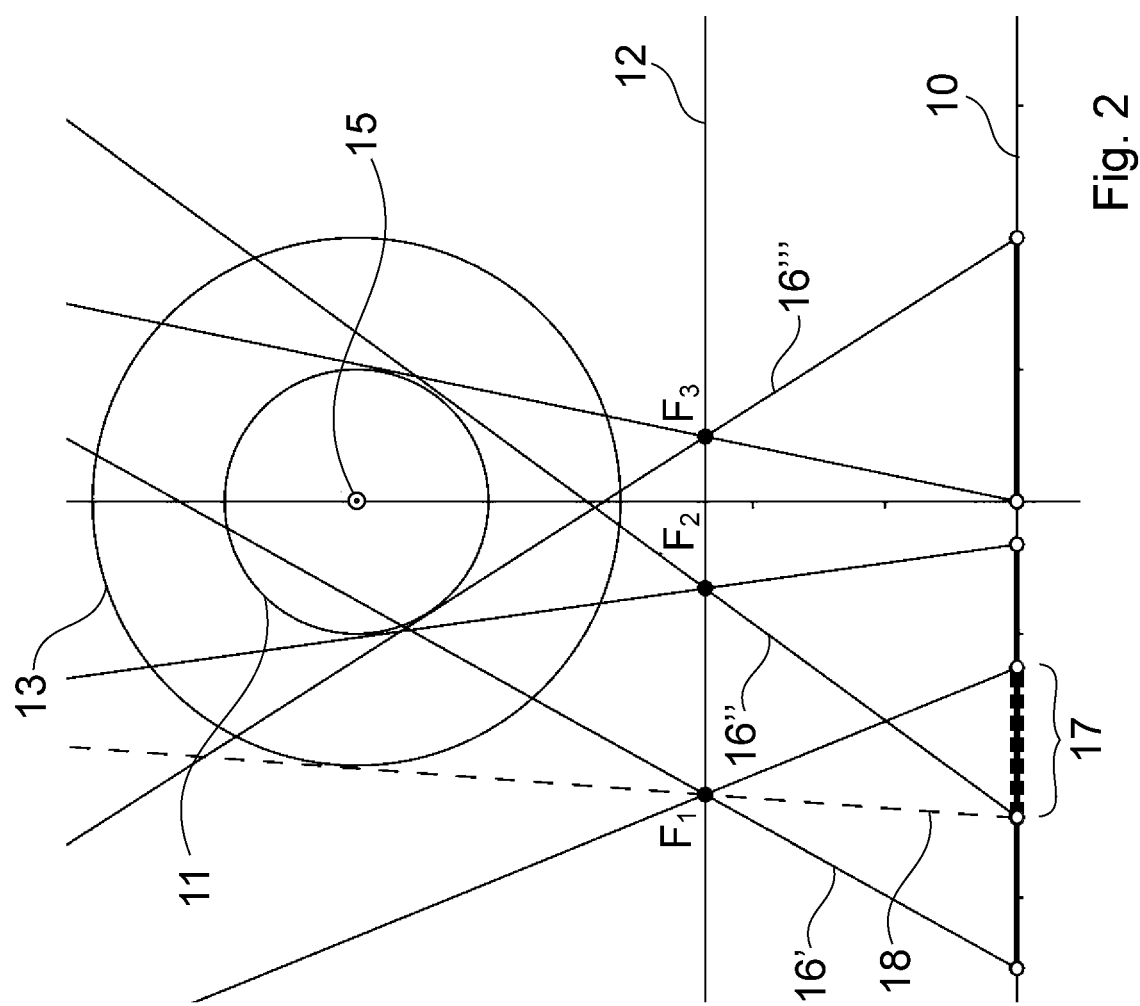
FIG. 2 illustrates, in transaxial view, an imaging according to an embodiment of the imaging device according to the invention.

Such a multi-region, overlapping imaging scheme being in line with the invention is shown in FIG. 2; in case of the projection of FIG. 2, as it is described below, the overlap is virtual. The pinhole characterised with the focal point $F_1$ (projection 16') projects the region outside the primary field of view 13 to a detector segment 17 denoted by dots (an auxiliary line 18 and the projection 16'' intersect each other on the detector 10), where by definition no activity can be found (the primary field of view 13 is defined such that it comprises all activity within its boundaries). The projection 16' projects a region of the primary field of view 13 possibly comprising some activity to a region lying to the left of the detector segment 17 in FIG. 2; and a portion of the central field of view 11 is also imaged by the projection 16'.

Compared to the conventional (non-overlapping) detector tiling (see FIG. 1) this imaging solution significantly improves the image characteristics of the imaging (see below for an explanation). Although the detector segment 17 denoted by dots significantly overlaps with the detector segment corresponding to the projection 16'' which corresponds to the focal point $F_2$, the imaging remains unambiguous (this is because the projection 16' contributes nothing to the imaging as it projects an activity-free region to the detector segment 17), and consequently no additional artifacts are generated when the imaging is reconstructed.

In the view shown in FIG. 2, the central field of view 11 is unambiguously and completely imaged by the pinholes characterised with the focal points $F_2$ and $F_3$ (see projections 16'' and 16'''). In the illustrated transaxial view, the area of the central field of view 11 is encompassed by the lines marking the edges of each of the projections 16'' and 16'''. As shown in FIG. 2, an overwhelming part of the primary field of view 13 is projected by the three projections 16', 16'', 16'''; while for completely projecting the primary field of view 13 additional pinholes are required.

The imaging scheme according to FIG. 2 has the additional advantageous feature that the lateral pinholes adapted for imaging a region lying outside the central field of view 11 but inside the primary field of view 13 perform projection to the lateralmost portions of the useful field of view of the detector 10, where the intrinsic resolution of the detector is typically poorer than in the central regions of the UFOV, and thus the solution according to the projection scheme presented herein allows that the central field of view 11 comprising the target region (the organ under examination) is imaged with the best possible imaging characteristics.

Since one of our objectives is to provide the highest sensitivity possible, during the design process it is expedient to place the focal plane (or surface) as close as possible to the object to be imaged (i.e. to the primary FOV and the CFOV encompassed therein). With certain geometrical configurations of the imaging setup the focal points of the so-called peripheral pinholes—situated at the lateral edges of the body of the collimator element in a transaxial view (transaxial peripheries), i.e. further from the longitudinal axis of the CFOV—would typically have to be moved closer to the so-called central pinholes adapted for imaging the CFOV compared to the position they would assume in case of a commonly applied, non-overlapping imaging. The reason for that may be, by way of example, that the collimator element typically has limited dimensions in the transaxial plane (the plane perpendicular to the field of view axis), with the exact dimensions being restricted by the number of applied imaging device units, the relative angles of view of the imaging devices and their radius of rotation (RoR, the radius along which the imaging devices are rotated in a SPECT apparatus), and in addition to that, all the pinholes adapted for imaging the primary FOV have to be physically accommodated on the collimator element.

In the context of FIG. 2 this means that there is a good chance that it is not possible to arrange the focal point $F_1$ in such a manner which would cause only a virtual overlap in the projection. Moving the focal point $F_1$ of FIG. 2 in the direction of $F_2$ (and thus the relocation thereof to a focal point $F_1'$ of FIG. 3) results in that an auxiliary line 22 that is shown in a dashed line in FIG. 3 (starting from the detector 10 at the edge of a projection 20" corresponding to the focal point $F_2$ and passing through the focal point $F_1'$) will intersect the primary field of view 13, and thereby this projection scheme generates a real overlapping projection in the regions situated near the transaxial extremities of the detector 10 (because a primary FOV region possibly comprising activity is projected to an overlapping detector segment 19 of the projections 20' and 20"). Such an overlapping projection is termed a partially overlapping projection.

Figure 3:
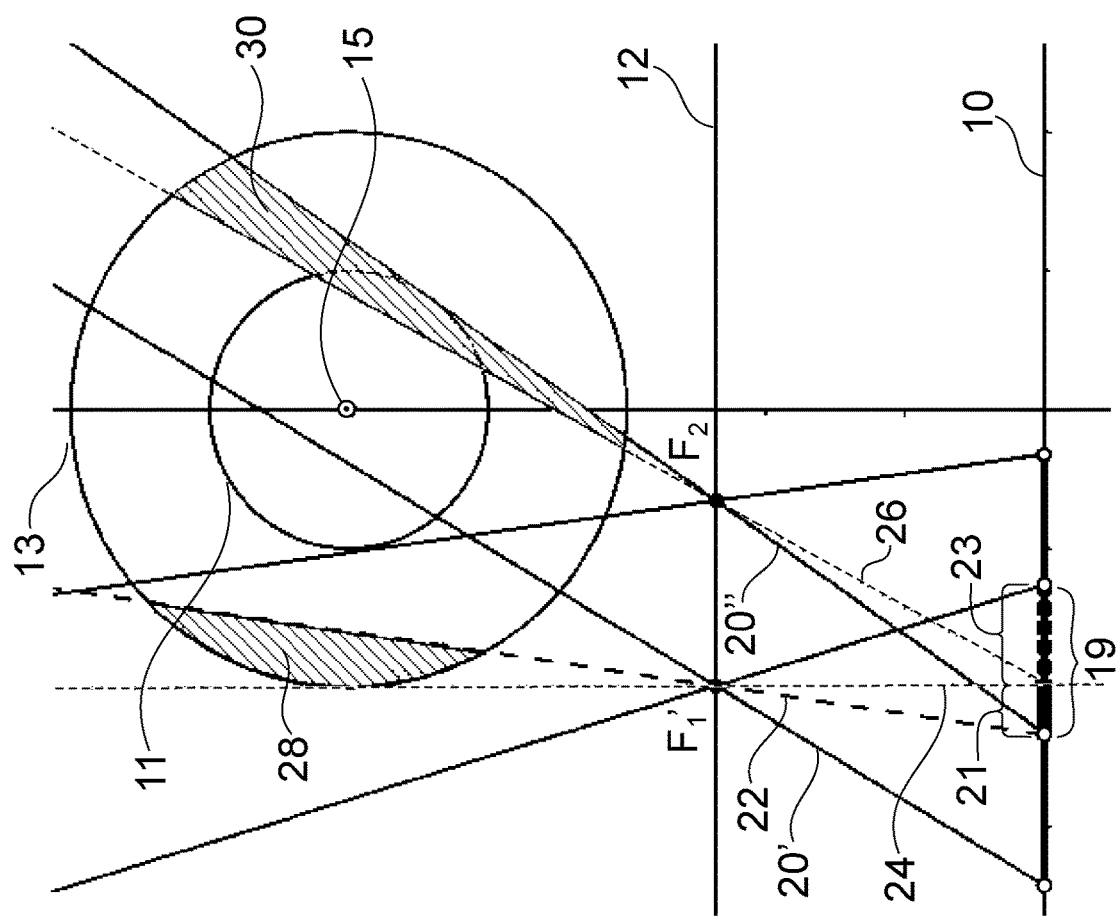
FIG. 3 illustrates, in transaxial view, an imaging realized with a further embodiment of the imaging device according to the invention.

In the detector 10 shown in FIG. 3 the partially overlapping region 21 (constituting a part of the overlapping detector segment) which introduces an inconsistency into the imaging of regions 28, 30 of the primary field of view 13 and of the central field of view 11, respectively, is denoted by a thick line. Depending on activity distribution, according to the literature this could result in generating by way of example ring-type artifacts (see for instance K. Vunckx et al., IEEE Trans. Med. Img., Effect of overlapping Projections on Reconstruction Image Quality in Multipinhole SPECT, vol. 27, no. 7, (2008)). In FIG. 3 an auxiliary line 24 extends along the boundary of the primary FOV and through a focal point $F_1'$. The detector segment 19 is divided into regions 21 and 23 by the intersection point of the auxiliary line 24 and the detector 10. There is a real overlap in the region 21, while the regions 23 comprise a virtual overlap, because a projection is performed to the region 21 of the detector 10 from inside the primary field of view 13. The projection 20" also projects to the region 21 from a region presumably comprising activity (i.e. from the region 30 which has parts extending into the central field of view 11). The region 30 can be defined using an auxiliary line 26 that—according to the edge of the overlapping region— starts at the intersection of the auxiliary line 26 and the detector 10 and passes through the focal point $F_2$. Applying the rules of projection it can be seen that the region 30 thus defined is projected onto the region 21.

In FIG. 3 the pinhole corresponding to the focal point $F_1'$ is shifted inward relative to the focal point $F_1$ of FIG. 2 such that the detector 10 region covered by the projection remains unchanged, i.e. the same detector 10 surface region is covered by the projection 16' and the projection 20' (accordingly, the detector segments 17 and 19 are coincident). In addition to that, the focal point $F_1$ has been brought closer to the focal point $F_2$ (thus obtaining the focal point $F_1'$), i.e. by the displacement of the focal point $F_1$ (with the projection region on the detector 10 kept fixed) the configuration of the pinhole is also changed, which causes the projection 16' to be transformed into the projection 20'. However, the focal point $F_2$ and therefore the projections 16" and 20" cover identical detector regions, with the respective pinholes corresponding to the focal point $F_2$ in FIGS. 2 and 3 having an identical configuration.

The projection 20' goes across the primary field of view 13 cutting a larger section than the projection 16', i.e. its boundary extends nearer to the boundary of the primary field of view 13, the projection 20' providing projection of a comparatively larger part of the primary field of view 13 and the central field of view 11 (by comparing FIGS. 2 and 3 it can be observed that a much greater portion of the central field of view 11 is imaged by the projection 20' than by the projection 16').

Figure 4:
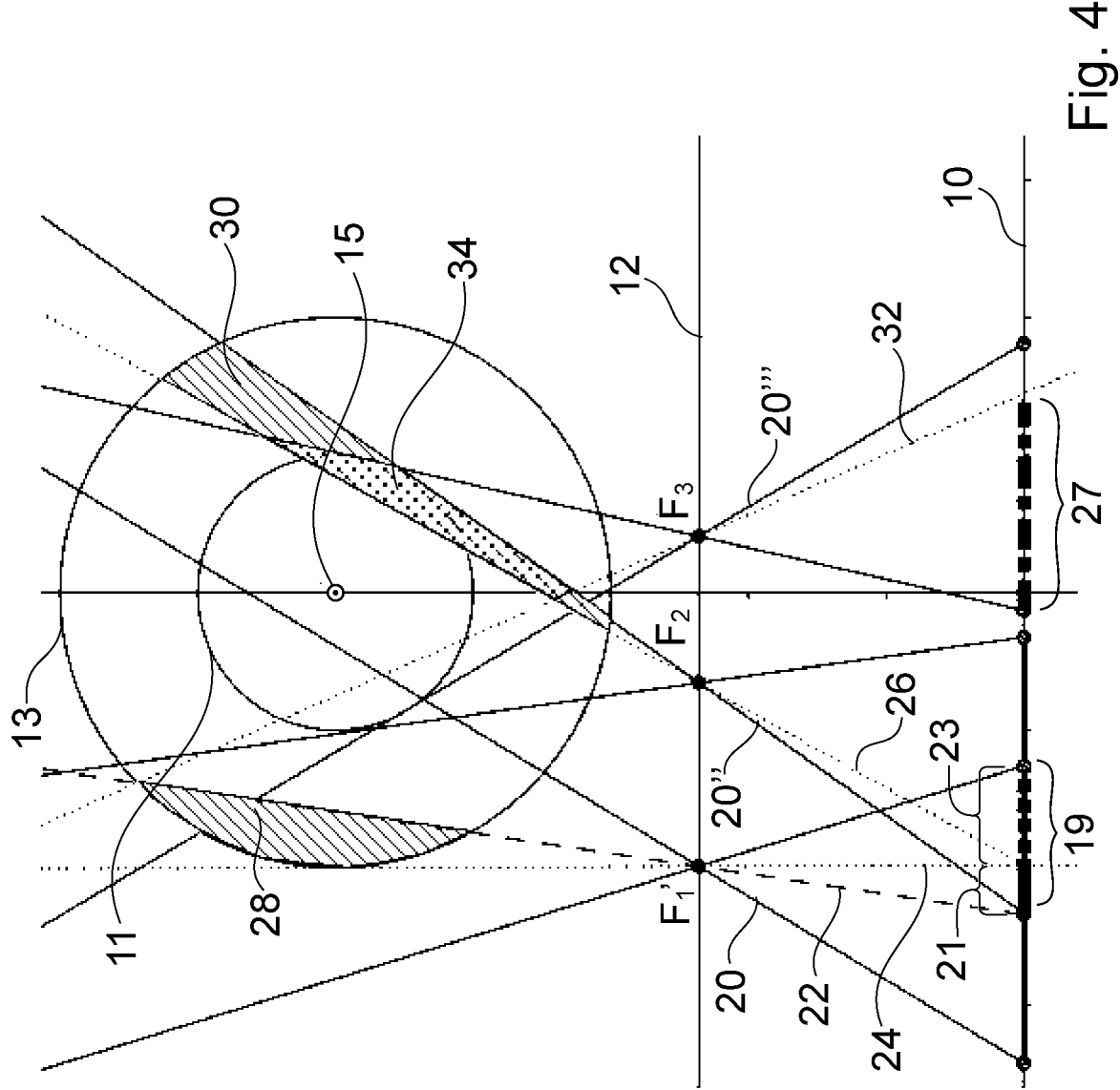
FIG. 4 illustrates, in transaxial view, an imaging realized with a yet further embodiment of the imaging device according to the invention.

However, if additional pinholes also have a view on the CFOV, the above mentioned ring artifacts can be completely eliminated from the CFOV, and their impact can be significantly reduced in the region inside the primary FOV but outside the CFOV. This is illustrated in FIG. 4 in the already shown transaxial view. According to FIG. 4, the central field of view 11 is completely imaged by the pinhole corresponding to a focal point $F_3$ (in the illustrated transaxial view the central field of view 11 is situated between the edges of the projection 20''' corresponding to the focal point $F_3$). Imaging inconsistency is resolved by the projection (imaging) 20''' in a part (in a region 34) of the region 30 of the primary field of view 13. The region 34 is denoted with a square grid pattern, while a detector segment 27 corresponding to the region 34 through the projection 20''' is designated with a dotted line. Since both regions 28 and 30 are partially projected by the portion of the detector 10 being outside the detector segment 27 corresponding to the projection 20''', this portion cannot by itself resolve the inconsistency caused by the overlap. This causes that with the given projection directions the linear equation system describing the projection cannot be solved unambiguously because it cannot be decided whether a given contribution originates from the region 28 or from the region 30. This does not mean that this inconsistency could not be resolved by applying other projections; the given spatial region can also be unambiguously imaged by one or more further pinholes from different directions, whereby the inconsistency can be resolved.

As shown in FIG. 4, the part of the region 30 situated inside the central field of view 11 falls entirely into the region 34. Accordingly, in the central field of view lithe projection inconsistency is completely resolved by the pinhole corresponding to the focal point $F_3$, and thus the region situated inside the central field of view 11 can be imaged in an artifact-free manner. In order to reconstruct the CFOV it is typically required that the CFOV and the primary FOV are imaged in a sufficient number of views (usually at least three but typically 8-16 views); to achieve that, more than one projections have to be recorded at different camera angles (a SPECT recording encompassing at least 180 degrees is typically required). This can be achieved by means of multiple fixed imaging devices arranged around the object to be examined, or by an imaging device that is rotated about the object to be examined.

According to the invention, therefore, artifact elimination in the CFOV is intended by applying the pinhole arrangement having the above described configuration. Contrary to general endeavours, according to the invention inconsistency is resolved only for the CFOV (i.e. a smaller region than the examined primary FOV) by having at least one pinhole unambiguously imaging the CFOV (i.e. projecting the CFOV onto an imaging region that does not overlap with any other imaging region). By the solution applying special partial overlaps on the detector according to the invention it can be provided that the CFOV can be reconstructed in an artifact-free manner due to the fact that the primary FOV is also imaged by pinholes focussed on the primary FOV. This is necessary because there can usually be found a significant amount of activity outside the CFOV but inside the primary FOV, and thus it is important that the reconstruction algorithm can take it into account. Besides that, the occurrence of artifacts in the region of the primary FOV situated outside the CFOV resulting from overlapping projection can preferably also be significantly reduced by resolving the inconsistencies (i.e. by providing a non-overlapping imaging of said region).

The imaging device according to the invention comprises a detector being adapted for determining a point of incidence of a—typically gamma—photon, and having an incidence surface, and a collimator element being adapted for projecting the photon on the detector, having an inlet surface, an outlet surface facing the incidence surface, and comprising pinholes connecting the inlet surface and the outlet surface.

1. In the device according to the invention the collimator element comprises one or more first pinholes being focussed on a central field of view (CFOV) having a cylindrical shape and having a field of view axis coincident with the axis of symmetry thereof.

In case the imaging device according to the invention is applied in a SPECT apparatus in which the imaging device is rotatable about the object being examined, the axis of symmetry of the central field of view, i.e. the field of view axis preferably coincides with the axis of rotation corresponding to the rotation.

Each first pinhole is adapted for projecting the central field of view onto one or more respective different first imaging regions (areas) (being different from each other) being on the incidence surface of the detector, and being non-overlapping with any other imaging regions, and, in case of more than one first pinholes, the first pinholes are arranged shifted with respect to one another in a direction parallel with the field of view axis.

The central field of view—and the primary field of view encompassing it—has a cylindrical shape since the imaging device (the unit comprising the detector and the collimator element) is typically rotated about the field of view, or recordings thereof are made by means of more than one imaging devices arranged at different sides, even at different radial positions. The field of view axis extends along the axis of symmetry (i.e. the longitudinal axis) of the cylindrical central field of view.

Therefore each first pinhole (or the single first pinhole if only one such pinhole is included) projects onto a respective corresponding first imaging region. These first imaging regions do not overlap with any other imaging region.

Preferably, more than one first pinholes are applied, and the first pinholes are shifted with respect to one another in a direction parallel with the field of view axis (in some embodiments the pinholes are shifted in such a manner that—together with other (second and third) pinholes—they form pinhole rows). An embodiment is also conceivable wherein the collimator element comprises only a single first pinhole. The reason for that can be that the central field of view is short in the direction parallel with the field of view axis, or that the single first pinhole is substantially able to image the entire central field of view also in the direction of the field of view axis. A reason why more than one first pinholes are preferably applied is that, having a view of the central field of view from slightly different angles they can provide slightly complementary imagings thereof in a direction parallel with the field of view axis.

A first pinhole substantially completely projects the central field of view viewed from the direction parallel with the field of view axis, that is its so-called transaxial projection (a projection onto the transaxial plane), transaxial view thereof. This manifests itself, if projections in these directions are shown, by that the entire central field of view is encompassed inside the boundaries of the projections (see e.g. in FIG. 13 projections 154a, 156a corresponding to pinholes 146a, 148a, and in FIG. 4 the projection 20''' corresponding to the focal point $F_3$).

2. The collimator element further comprises one or more second pinholes being focussed on the central field of view, being arranged on the collimator element in a respective position that is shifted with respect to the one or more first pinholes in a direction perpendicular to the field of view axis.

Each second pinhole is adapted for projecting the central field of view onto one or more respective different second imaging regions being on the incidence surface of the detector, and, in case of more than one second pinholes, the second pinholes are arranged shifted with respect to one another in a direction parallel with the field of view axis.

The one or more second pinholes are therefore shifted with respect to the one or more first pinholes in a direction perpendicular to the field of view axis (as shown in the figures, this shift direction is parallel with the collimator—and thus the surfaces thereof connected by the pinholes—and is also perpendicular to the field of view axis, i.e. it is a direction perpendicular to the projection of the field of view axis on the collimator element), so—if there are more than one second pinholes—they form a pinhole column that is shifted relative to the preferably more than one first pinholes. The pinholes are usually arranged in multiple columns on the collimator element. The pinhole columns are parallel with the field of view axis, (and thus with its projection on the collimator element), while the pinhole rows are perpendicular thereto (and so also to the columns).

A second pinhole, viewed from the direction parallel with the field of view axis, does not necesserily project completely the central field of view, i.e. its transaxial projection, transaxial view, only at least partly, preferably a major part thereof. When illustrating the projections this is manifested as when projections from these directions are shown the central field of view is not completely encompassed by the projection boundaries but at least one boundary goes across (crosses, intersects) the central field of view (cutting a typically a small section, i.e. it passes near the boundary of the central field of view). The other projection boundary typically extends along the outside edge of the central field of view, but may also goes across the central field of view cutting a small section (see for example in FIG. 13 a projection 156*b* corresponding to the pinhole 148*b*; in FIG. 4 the projection 20″ corresponding to the focal point $F_2$ is also obtained with a second pinhole, but in the given view the central field of view 11 is encompassed within the boundaries of the projection 20″).

Preferably, more than one second pinholes are applied, the second pinholes being shifted with respect to one another in a direction parallel with the field of view axis; the second pinholes form a second pinhole column. Such an embodiment can also be conceived which comprises only a single second pinhole.

3. The collimator element further comprises one or more third pinholes being focussed on a primary field of view having a cylindrical shape, encompassing the central field of view and having a longitudinal axis coincident with the longitudinal axis of the central field of view. The one or more third pinholes are preferably formed in the collimator element in a respective position that is shifted with respect to the one or more second pinholes in a direction perpendicular to the field of view axis.

Each third pinhole is adapted for projecting the primary field of view on one or more respective different third imaging regions being on the incidence surface of the detector, each of one or more third imaging regions overlap with at least one second imaging region (preferably with the subregion thereof lying proximate the edge of the detector), and, in case of more than one third pinholes, the third pinholes are arranged shifted with respect to one another in a direction parallel with the field of view axis.

A third pinhole, viewed from the direction parallel with the field of view axis, projects the primary field of view, i.e. its so-called transaxial projection, transaxial view not necessarily completely, only preferably as big a part as possible, i.e. at least partially. For depicting the projections this manifests itself in that one of the boundaries of the projection passes near the boundary of the primary field of view (taken in the particular projection), while the other boundary goes across the primary field of view, cutting a section thereof of a non-negligible size. There are a number of reasons for that.

On the one hand, the best possible imaging of the primary field of view is intended to be provided by the help of the pinholes altogether, i.e. such portions of the primary field of view which fall into the projections provided by the first and second pinholes are imaged by these pinholes, thereby complementing the imaging provided by the third pinhole. On the other hand, typically each second and third pinhole has such a counterpart which is arranged symmetrically to the column of first pinholes (i.e. the collimator element typically has a symmetrical configuration), with another major portion of the corresponding projection of the primary field of view also being imaged by this counterpart of the given pinhole (typically, there is of course an overlap between the respective projections of the two third pinholes). A projection 156*c* of the pinhole 148*c* (belonging in the category of third pinholes) is shown in a transaxial view in FIG. 13; it is arranged such that one of the boundaries of the projection 156*c* passes just outside the edge of a primary field of view 142, but its other boundary goes across the primary field of view 142, cutting a quite large section. In FIG. 4 the pinhole corresponding to the focal point $F_1$ is a third pinhole, with one boundary of the projection 20′ provided by it passing—in the view shown in the figure—outside the edge of the primary field of view 13 at a certain distance, and the other boundary thereof going across the primary field of view 13 cutting a section of considerable size. In FIGS. 1-4 there is shown a field of view axis 15 (extending perpendicular to the plane of the figure).

The third imaging region corresponding to each third pinhole overlaps with at least one (in a number of embodiments only one but in certain embodiments more than one) second imaging region. An overlapping projection between the second and third imaging regions is therefore provided.

Preferably, more than one third pinholes are applied, the third pinholes being shifted with respect to one another in a direction parallel with the field of view axis; the third pinholes form a third pinhole column. Such an embodiment is also conceivable which comprises only a single third pinhole.

Figure 14:
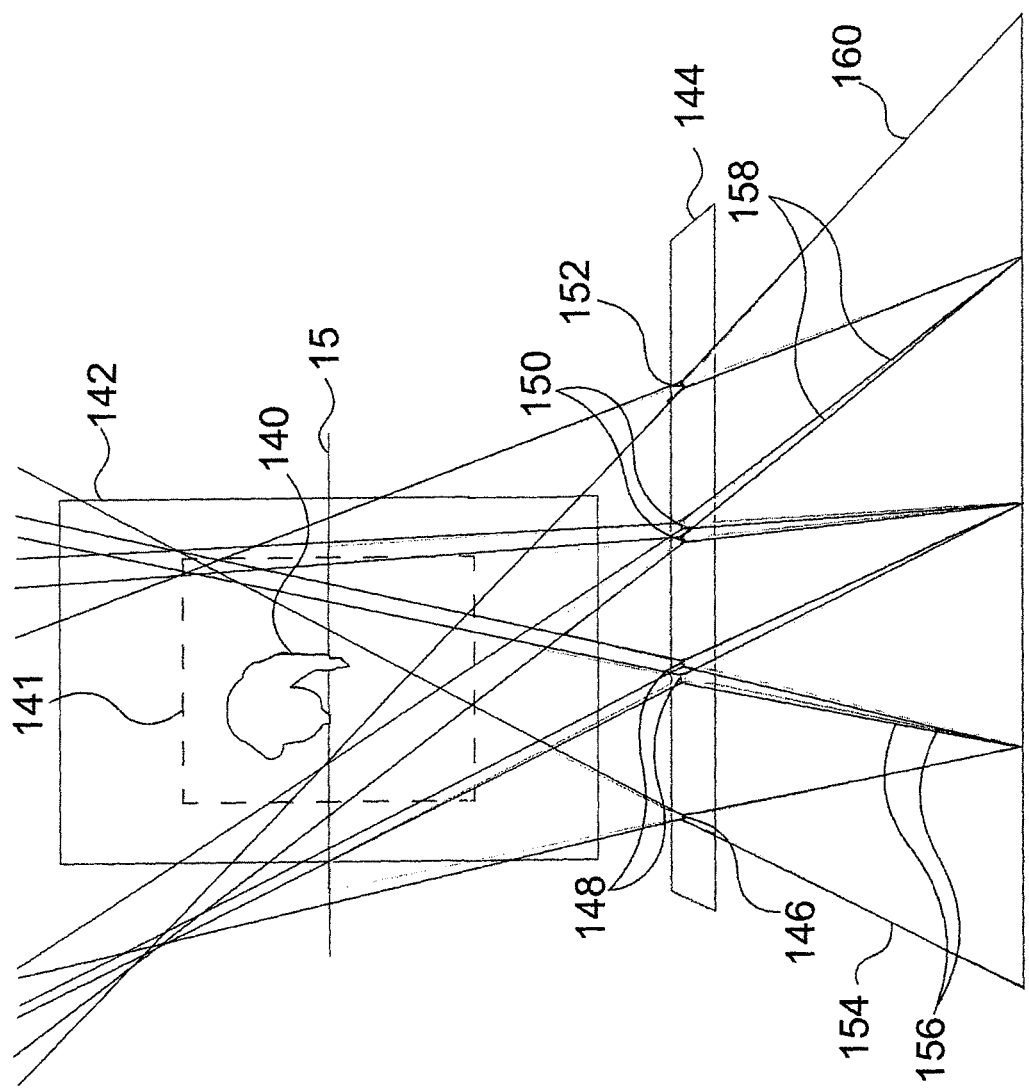
FIG. 14 is a drawing illustrating the imaging of FIG. 11 in side view.

As illustrated also in FIG. 14, each individual pinhole is typically capable of imaging the given field of view only to a certain extent in the axial direction (in a direction parallel with the field of view axis), i.e. in the axial view perpendicular to the transaxial view they provide imaging of only a particular portion thereof. Therefore, preferably multiple pinholes of the same type (i.e. first, second, or third pinholes), shifted in the axial direction relative to one another, can be applied in order that the axial view of the CFOV/FOV can be covered by the projections as completely as possible in the axial view. In the transaxial view, the entire given field of view can be covered by, by way of example, the first pinhole. In the transaxial view, the first and second pinholes corresponding to one another (i.e. situated in the same row) provide projections of preferably overlapping, but particularly preferably substantially coincident portions of the central field of view, the third pinhole providing the same for the primary field of view (cf. FIG. 14; the portion of the FOV covered by the projection of the third pinhole, extending into the CFOV, overlaps with the former portions). In an embodiment, in a transaxial view (i.e. considering the transaxial view) at least 70% (preferably 90%) of the transaxial view (projection) of the primary field of view (primary FOV) is collectively projected onto the detector by the one or more first pinholes, the one or more second pinholes and the one or more third pinholes.

According to the above, the first, second and third pinholes are focussed on either (the central or the primary) one of the fields of view. By this it is meant that one or both boundaries of the projection realized by the focussed pinhole pass near the edge of the given field of view in transaxial view.

A pinhole is called "focussed on the CFOV" if in the transaxial view it is true that the boundary lines defining the projection region (such as, e.g., the boundary lines of the projection 16″ of FIG. 2; see also the boundary lines of the projection 156*b* of FIG. 16, based on which also the projection 156*b* can be considered focussed on the central field of view 141) typically pass near the circle representing the CFOV in the transaxial view. The boundary lines therefore constitute the edges or boundaries of the projection in the transaxial view. Preferably, it is true for all these boundary lines (in the transaxial view, for both) that the distance of these lines from the circle representing the CFOV in the transaxial view is smaller than 70%, particularly preferably 30%, of the circle's radius, in a particularly focussed still more preferred case, smaller than 10% of the radius of the circle. These values preferably hold true in case the pinholes are focussed on the FOV, but in case of the FOV it is sufficient if this proximity condition is fulfilled only for one of the boundary lines.

As regards the projections of at least one (or all) of the one or more first pinholes it preferably holds true—for each individual projection—that more than 70%, particularly preferably 90%, still more preferably 95% of the area of the circle representing the CFOV in transaxial section falls inside the boundary lines of the projection.

As regards the projections of at least one (or all) of the one or more second pinholes it preferably holds true—for each individual projection—that more than 50%, particularly preferably 75%, still more preferably 90% of the area of the circle representing the CFOV in transaxial section falls inside the boundary lines of the projection.

As regards the projections of at least one (or all) of the one or more third pinholes it preferably holds true—for each individual projection—that more than 20%, particularly preferably 35%, still more preferably 50% of the area of the circle representing the FOV in transaxial section falls inside the boundary lines of the projection.

The size of an overlap region corresponding to the overlap between a second imaging region and a third imaging region is preferably 10-60%, particularly preferably 20-50%, particularly still more preferably 30-50% of the area (surface area) of the bigger one (if the two are equal in size, any one) of the given second and third imaging regions.

The boundaries of the projection can be established based on the configuration of the pinholes (i.e. focal point, inlet and outlet apertures thereof), the projections are represented in the figures illustrating the invention by showing the boundary lines thereof. For the third pinholes only looser (lower-degree) focussing is required but naturally—because for adjusting the pinholes it is a primary consideration that they are adjusted such that the projections provided by them go across the primary field of view cutting as large a section as possible, otherwise the given pinhole arrangement would make no sense—all third pinholes are focussed on the primary field of view. Accordingly, the third pinholes are focussed on the primary field of view, and are primarily adapted for imaging the activity situated in the primary field of view (rather than that of the central field of view), however it is not disadvantageous if they also image as large a portion of the central field of view as possible, since thereby they provide an additional view also of the central field of view for the reconstruction.

To sum up the above, it can be stated that in the imaging device according to the invention the application of such first type pinhole (first pinhole) is necessary, which project the CFOV on the detector in a non-overlapping manner—and, to a good approximation, completely—as far as the transaxial view (i.e. a view taken perpendicular to the field of view axis) thereof is concerned. In a transaxial view this first type pinhole is directed substantially to the CFOV, i.e. to the region encompassing the activity to be examined, that is, it is focussed on the CFOV. By that it is meant that in the transaxial view the projection covers the region defined by the CFOV as completely as possible (it is also conceivable that certain negligible external regions of the CFOV are not imaged, and that the projection line passes slightly further from the boundary of the CFOV than what is shown in FIG. 4). The detector is situated at a fixed distance from the collimator element.

It is also necessary to apply such a second type pinhole (second pinhole) that is substantially directed to the CFOV and images as large part thereof as possible on the detector. In case a second pinhole is situated around the first pinhole at each side thereof, the second pinholes may for example be adjusted such that they are focussed on the CFOV from both sides; the pinhole on one side projects to a larger extent one side of the CFOV, and the pinhole on the other side projects to a larger extent the other side thereof. Then, the respective outside "edges" of the projections typically run near the boundaries of the CFOV. A second type pinhole projects onto the detector overlapping with a third type pinhole (third pinhole) that is directed to the region of the primary FOV situated outside the CFOV. Projections corresponding to the third type pinholes typically extend near the outside boundary of the primary FOV; the third type pinholes are not intended to cover as large a part of the CFOV as possible, however, these pinholes may also contribute to imaging the region inside the CFOV as favourably as possible.

Figure 5:
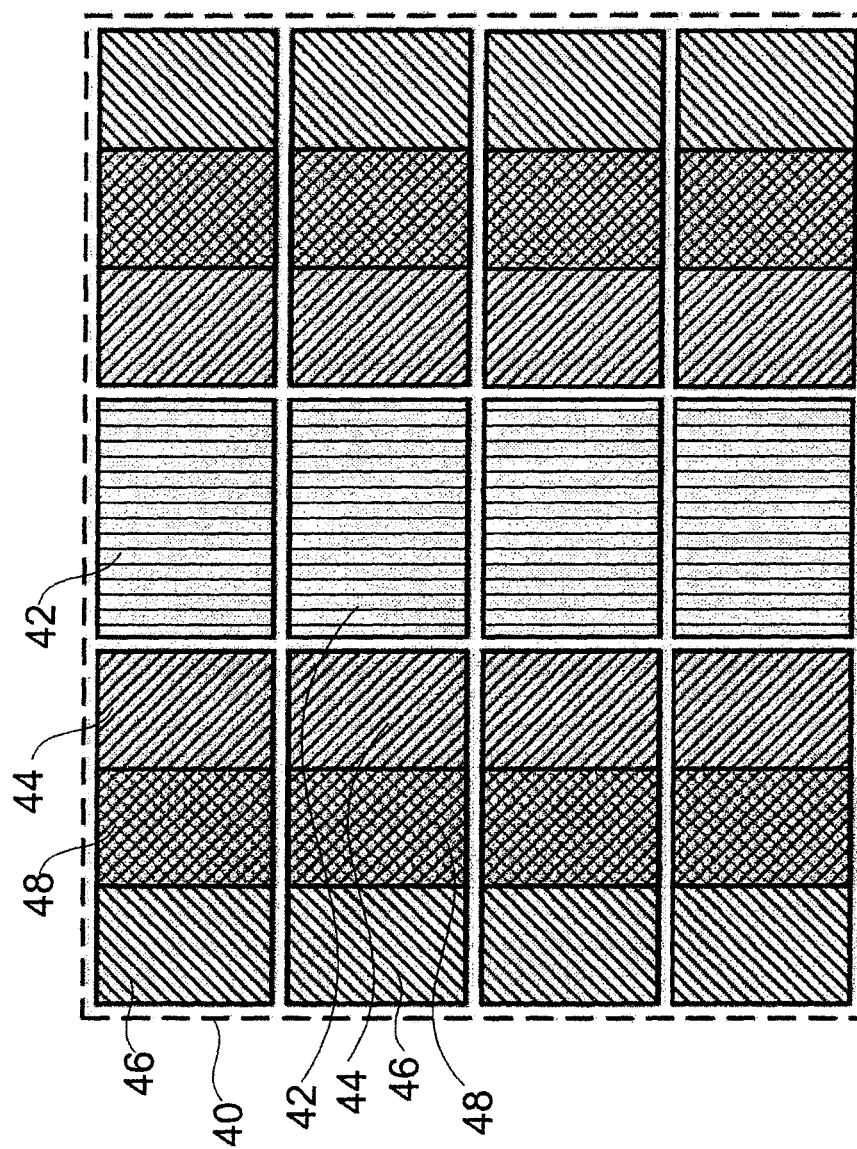
FIG. 5 illustrates the arrangement of the imaging regions on the detector according to an embodiment.
Figure 8:
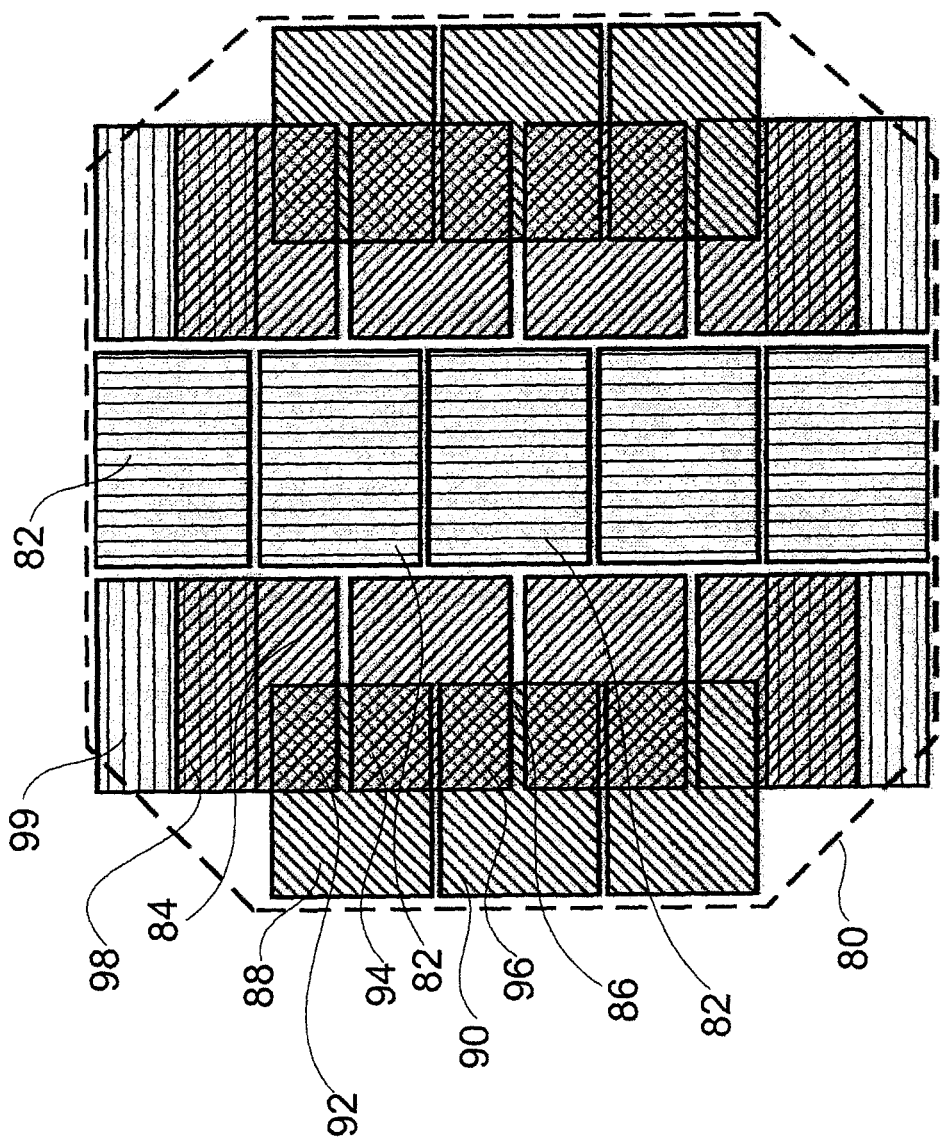
FIG. 8 illustrates the arrangement of the imaging regions according to a further embodiment.
Figure 9:
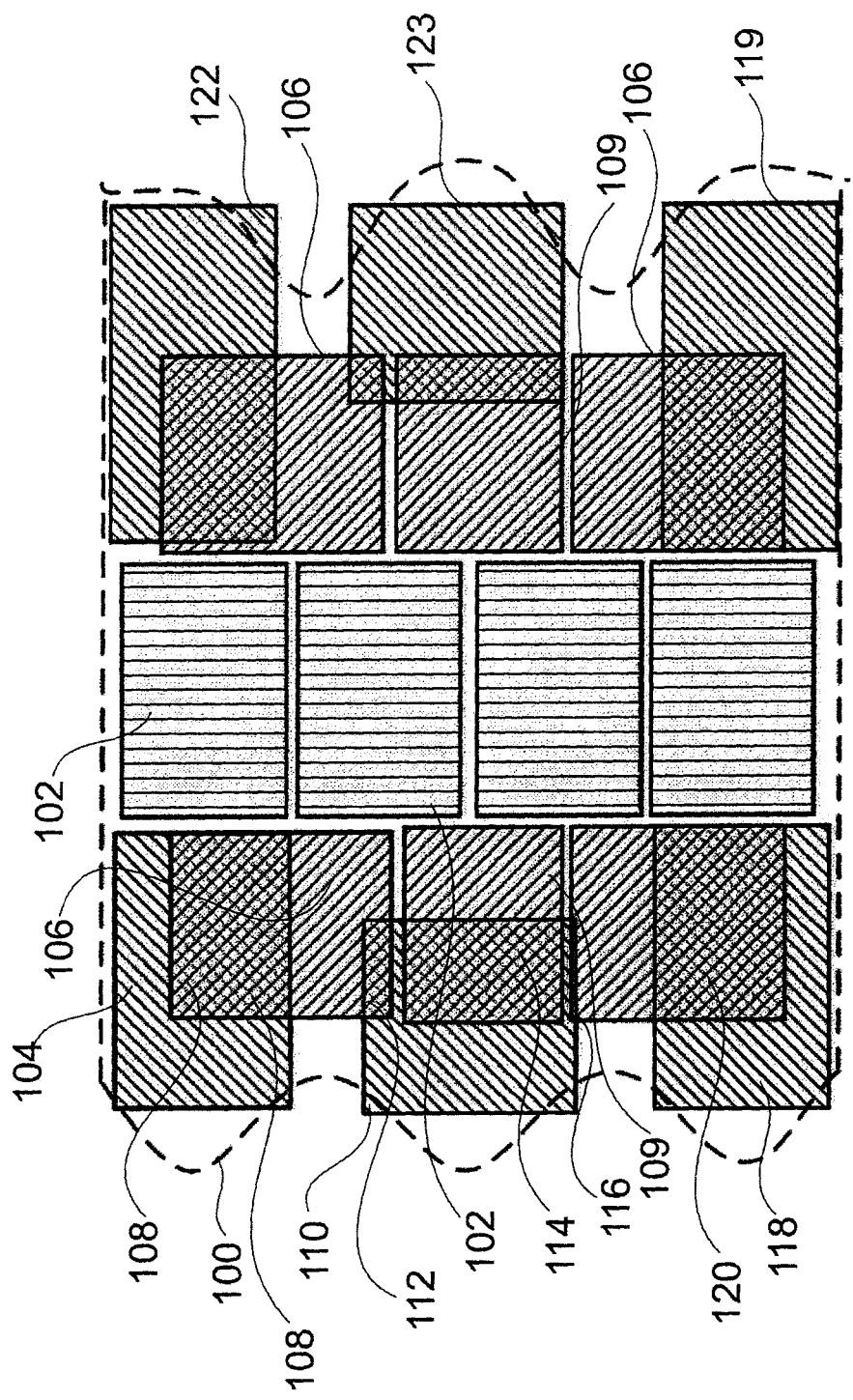
FIG. 9 is a schematic drawing showing the layout of the imaging regions on a detector having a useful field of view with wavy edges.
Figure 10:
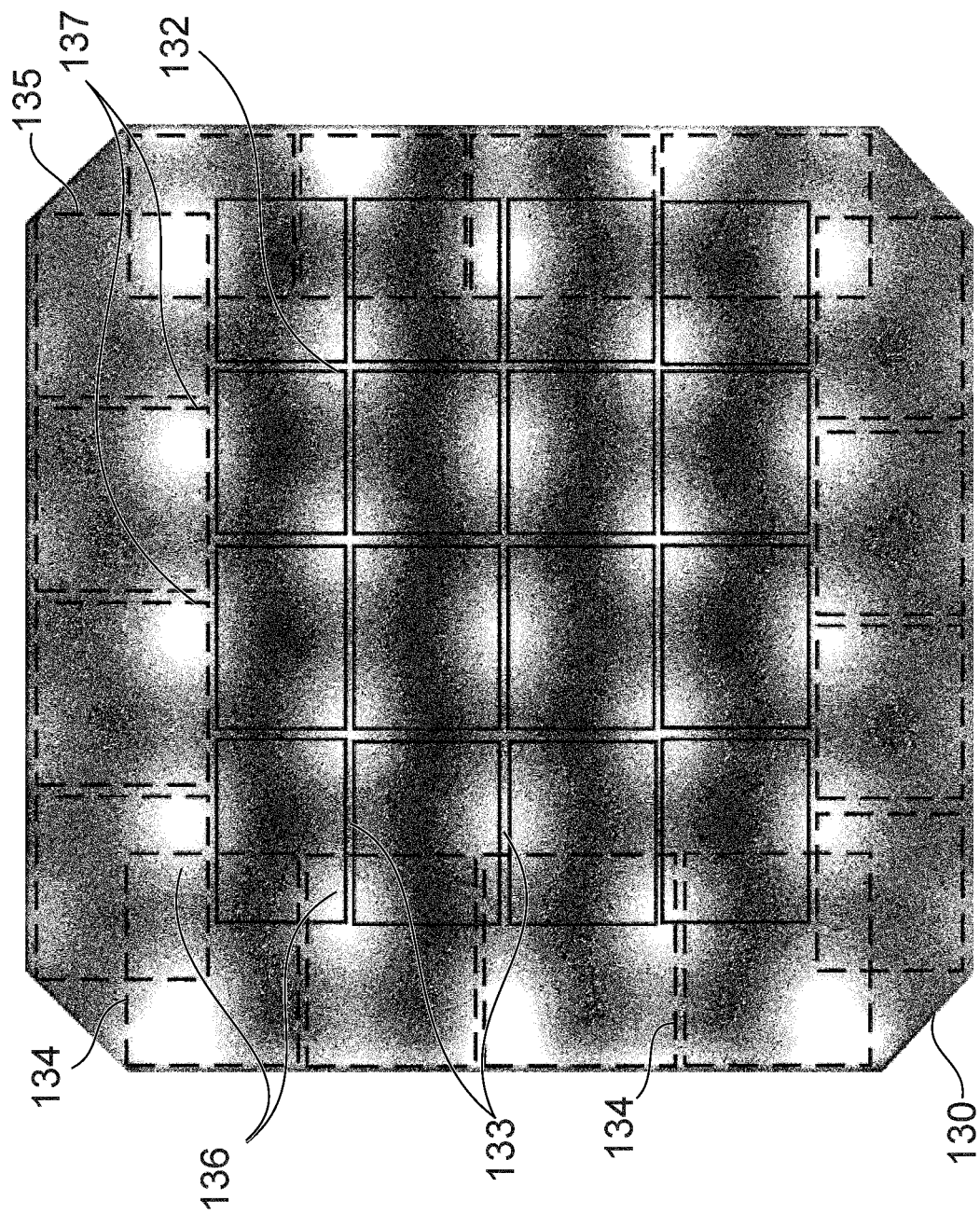
FIG. 10 illustrates the arrangement of the imaging regions according to a yet further embodiment, also showing the detecting (intrinsic) resolution distribution of the detectors.

In FIGS. 5-9—and essentially in FIG. 10, too—such segmentations (sectioning, partitioning) of the useful field of view of the detector are presented which are obtained in line with what has been set forth above (such divisions of the detector's useful field of view are primarily suited for illustrating the projections). In case the useful field of view has a rectangular shape (due to a rectangular mechanical shading or electronic iris), the detector segmentation according to an embodiment of the invention that can be made to correspond to the partially overlapping projection shown in FIG. 4 in the simplest way is shown in FIG. 5, where the boundary of a useful field of view 40 is designated by dashed lines.

In the embodiment illustrated in FIG. 5 non-overlapping imaging regions 42 are located in the centre of the detector according to the figure, and partially overlapping projections are situated on the left and on the right. The partially overlapping projections are produced between a second imaging region 44 projected from a second pinhole and a third imaging region 46 projected from a third pinhole. Between the left-slanted hatched second imaging region 44 and the right-slanted hatched third imaging region 46 there is produced an overlap region 48 designated with a square pattern.

The pinhole arrangement corresponding to the imaging regions 42, 44 and 46 cannot be found out from FIG. 5, which shows only the segmentation of the useful field of view 40 situated on the incidence surface of the detector (this also applies, mutatis mutandis, to FIGS. 6-10). As shown in FIG. 5 the imaging regions 42 corresponding to the first pinholes form a column of four pinholes (the imaging regions 42 are arranged at regular intervals in a direction parallel with the field of view axis; the direction of the field of view axis being vertical in the view illustrated in the figure, identical with the direction of the column the of imaging regions 42); the first pinholes providing projections on the first imaging regions 42 preferably also forming a column of first pinholes.

On both sides of the column of the imaging regions 42, there are located columns of the imaging regions 44. These regions are imaged by a respective column of second pinholes that are preferably also situated at both sides of the column of first pinholes. The imaging regions 46 overlap with the imaging regions 44, with the columns of the imaging regions 46 being situated at the left and right sides of the figure, overlapping with the columns of the imaging regions 44. Projection on each column of the imaging regions 46 is provided by a respective column of third pinholes.

The imaging regions 46 therefore correspond to projections focussed on regions situated outside the CFOV that overlap with the projections corresponding to the imaging regions 44 which are already focussed on the CFOV. Besides that, the CFOV is imaged to the imaging regions 42 unambiguously, in a non-overlapping manner.

The useful field of view 40 of the detector is optimally filled by the imaging regions 42, 44 and 46. The imaging regions 42, 44 and 46 are rectangular, i.e. they are obtained as a result of projections performed by pyramidal-shaped pinholes. Projections on a rectangular useful field of view 40 can be most expediently provided applying pyramidal pinholes.

In an embodiment of the imaging device according to the invention therefore the one or more first pinholes, the one or more second pinholes, and the one or more third pinholes have a pyramidal configuration. Such an embodiment is also conceivable wherein the different type pinholes (first, second, third) are configured differently, e.g. one type is pyramidal and the other is conical, but such arrangements are not expedient, since the objective is to completely cover the detector, retaining the possibility to adjust the overlaps independent of that, which can be performed in a most preferred manner if pinholes of identical configuration are applied in the collimator element. However, it has to be emphasised that the imaging device according to the invention can be implemented not only with pyramidal pinholes but the imaging apparatus can also be implemented—adhering to the principles according to the invention—by arranging conical (circular cross-section) or e.g. hexagonal (hexagonal cross-section) pinholes in the collimator element.

Figure 6:
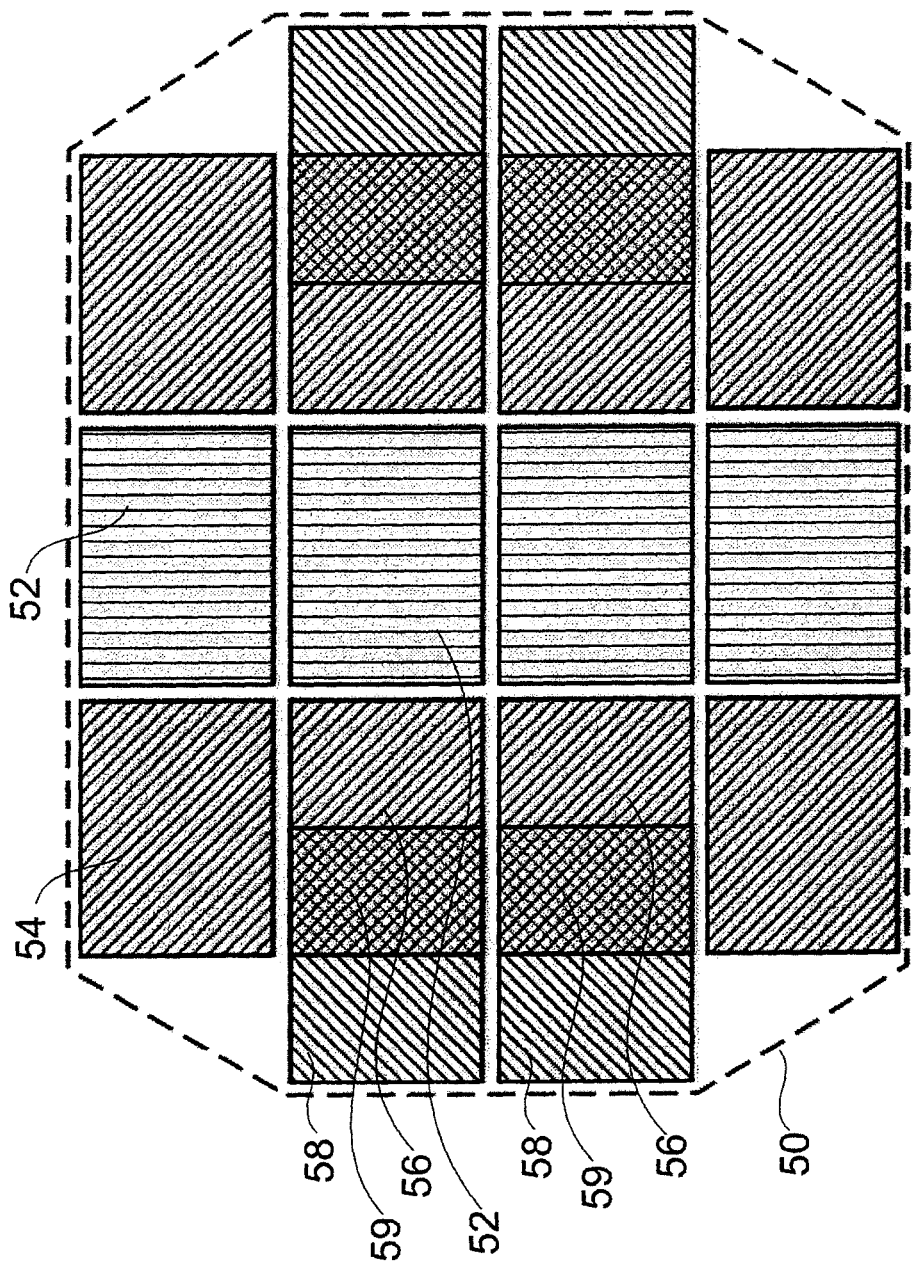
FIG. 6 illustrates the arrangement of the imaging regions according to a further embodiment.
Figure 7:
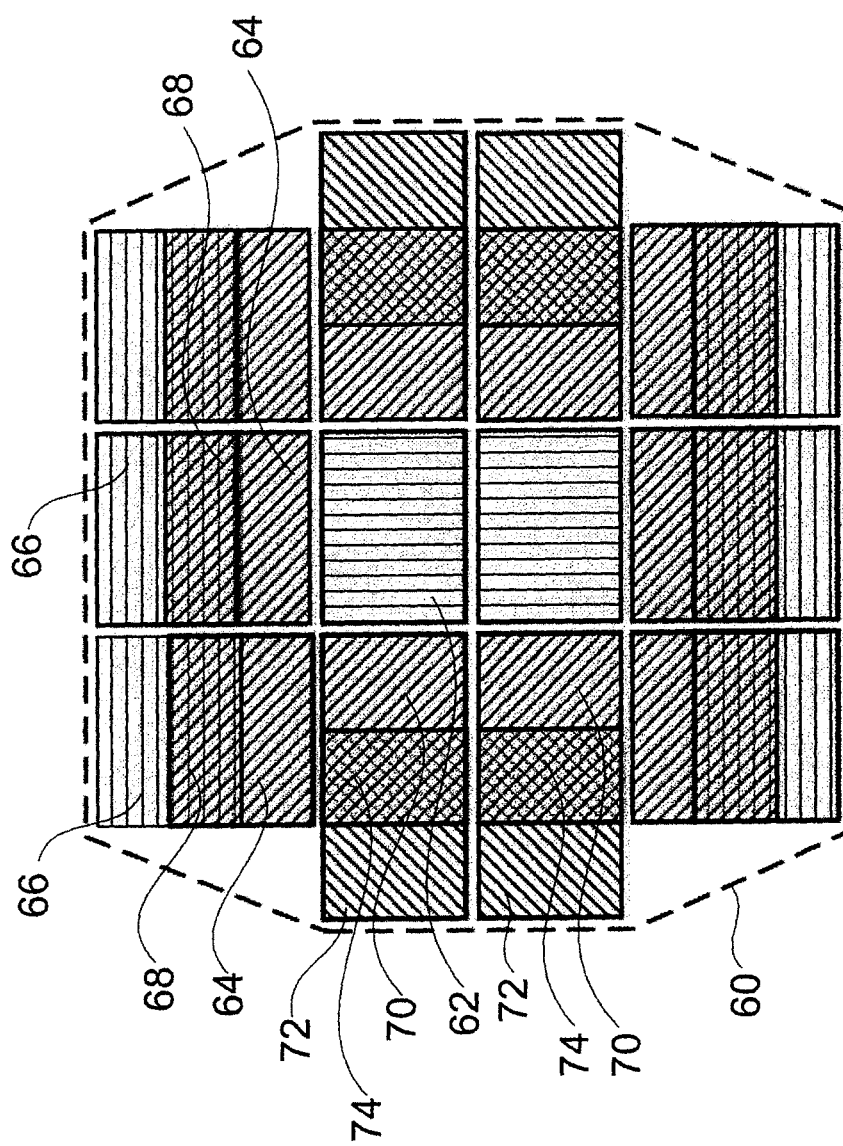
FIG. 7 illustrates the arrangement of the imaging regions according to a yet further embodiment.

In FIG. 6 a segmentation of detector's the useful field of view corresponding to a further embodiment of the imaging device according to the invention is shown. In this embodiment a useful field of view 50 of the detector has a shape of a rectangle with cut corners (truncated, rounded-off rectangle), and third imaging regions 58 are arranged exclusively along straight line segments extending between the cut corners. It is noted that the embodiments shown in FIGS. 7, 8 and 10 are also similar in this respect; these embodiments—as it is also illustrated in the figures—have the common feature that in the "corners" (i.e. at the truncated corners of the detector's field of view) there are no imaging regions, that is, no pinholes projects on these regions; therefore such pinholes which would provide projections on the corners can be omitted.

As opposed to the columns formed by the first and second pinholes, in the arrangement according to FIG. 6 each column of third pinholes consists of only two members (i.e. altogether four pinholes). Of the pinhole rows only the second and third rows (counted in a direction parallel with the field of view axis) comprise pinholes of the first, second and third type, the first and last rows not comprising second and third pinholes because there is no overlap.

This is particularly preferable if in the given embodiment the detector is implemented with photodetectors, for example, photomultipliers arranged in a hexagonal grid. As it was described in detail above, the detector preferably comprises a scintillation crystal and, arranged beside it on the side opposite to the incidence surface, preferably also comprises photomultipliers.

With such a hexagonal-grid PMT arrangement the image quality and resolution is often much lower in the corners of the detector than in the central part and at the vertical and horizontal peripheries (according to FIG. 6) of the useful field of view. Therefore in certain detector constructions the projections adapted for imaging regions lying outside the CFOV (i.e. the primary field of view) which would provide projections to the corners can be omitted, moreover, their omission may improve the characteristics of the imaging. Since in these imaging regions only noisy, bad-quality images could be recorded, the deterioration of overall image characteristics due to the noise introduced by such regions would outweigh the advantages of additional information provided by them.

Such an arrangement is therefore presented among others in FIG. 6 wherein the boundaries of the useful field of view 50 designated by dashed lines are truncated at the corners. In this embodiment, first imaging regions 52 are arranged in the centre of the useful field of view 50 extending parallel with the field of view axis. These regions are arranged analogously with the imaging regions 42 and also image the central field of view in a non-overlapping manner. In this embodiment, however, such imaging regions 54 are situated at the axial ends of the useful field of view 50 (i.e. at the field of view axis-direction extremities of the useful field of view of the detector: at the top and at the bottom of the figure) which cannot be classified into the group of second imaging regions because they do not overlap with any third imaging regions.

On each side of the first imaging regions 52 there are arranged two second imaging regions 56 that are therefore adapted for imaging the central field of view overlapping with the third imaging regions 58; accordingly an overlap region 59 is formed between each of the second imaging regions 56 and third imaging regions 58.

The third imaging regions 58 are situated near the edges of the useful field of view 50 of the detector, and along a straight segment of said edges. Typically, the third imaging regions are situated at the edge of the useful field of view of the detector, since it would not be expedient to arrange the third imaging regions (i.e. the lateralmost imaging regions) such that there is left an unused detector area between the third imaging region and the edge of the useful field of view.

FIGS. 11-14 also belong to this embodiment, with the collimator element and the arrangement of the pinholes therein corresponding to the present imaging region layout being shown in them together with the projections.

In this embodiment the configuration of the imaging regions 54 (which according to FIG. 6 do not overlap with any other imaging region) is preferred also due to the following. Those rows of pinholes (the first and last row) which provide projections onto the adjacent imaging regions 54-52-54 (in these rows these regions are non-overlapping) are preferably adapted for imaging such subregions of the primary field of view and the central field of view which are situated proximate the axial-direction extremities of the given field of view. In case, therefore, the pinhole focussed on the primary field of view is omitted from this row of pinholes almost no information is lost, because the primary field of view can be satisfactorily imaged applying the remaining pinholes. Omitting the imaging regions 58 at the corners of the detector's field of view the overall signal-to-noise ratio of the imaging typically improves (the imaging region layout shown in FIG. 6 is obtained from the one shown in FIG. 5 by omitting the imaging regions situated at the corners, i.e. by not providing projections on these regions). At the same time, as it is illustrated also by FIG. 14, in a manner different from other rows, projections of the central field of view on the imaging regions 54 located in these rows are provided in a non-overlapping manner, which projections can yield additional valuable information on the most relevant central field of view.

An imaging region layout corresponding to a further embodiment of the invention is illustrated in FIG. 7. As it has been mentioned, in the embodiment according to FIG. 7—in a manner similar to the embodiment of FIG. 6—there are no imaging regions in the omitted corners of a useful field of view 60, and third imaging regions 72 are located along straight segments of the edge of the useful field of view 60.

In addition to that, in an embodiment the collimator element further comprises
- a first supplementary pinhole being arranged in a position shifted with respect to the lateralmost of the one or more first pinholes and/or one or more second pinholes and/or the one or more third pinholes in a direction parallel with the field of view axis and being adapted for projecting the central field of view on a first supplementary imaging region being on the incidence surface of the detector, and
- a second supplementary pinhole being arranged in a position shifted with respect to the first supplementary pinhole in a direction parallel with the field of view axis and being adapted for projecting the primary field of view on a second supplementary imaging region overlapping with at least one first supplementary imaging region (preferably with a part thereof lying proximate the edge of the detector) and being on the incidence surface of the detector.

Such an embodiment is the one illustrated in FIG. 7, which shows that second imaging regions 70 overlapping with a respective third imaging region 72 in overlap regions 74 are arranged on both sides of the column (having two members) of first imaging regions 62 imaging the central field of view. Each of the first, second and third pinhole columns corresponding to the imaging regions 62, 70 and 72 has two members. The further imaging regions of the embodiment according to FIG. 7 cannot be classified as either first, second or third imaging regions; thus, as set forth above, they are termed first supplementary imaging regions 64 and second supplementary imaging regions 66.

In the embodiment shown in FIG. 7 the supplementary imaging regions 64, 66 are arranged at the extension (elongation) of the columns of the first and second imaging regions 62 and 70, respectively, i.e. beside the lateralmost first and second imaging regions 62, 70. Because each column comprises two imaging regions 62, 70, all of these regions are lateralmost and therefore there is a supplementary imaging region beside each. In principle, supplementary imaging regions could be arranged in the extensions of the columns formed by the third imaging regions 72, but these regions would be small-sized even without truncating the corners of the useful field of view 60, and in a disadvantageous manner, would doubly overlap with the imaging regions 64, 66, and 68. On the other hand—if photomultipliers (or other photodetectors) arranged in a hexagonal grid are applied—these portions of the detectors have intrinsically inferior imaging characteristics anyway.

The first supplementary imaging region 64 and the second supplementary imaging region—and preferably also the first and second supplementary pinholes corresponding thereto—are shifted relative to each other in a direction parallel with the field of view axis. The imaging regions 64 and 66 overlap in an overlap region 68. The first supplementary imaging region 64 is adapted for projecting the (corresponding parts of) the central field of view and the second supplementary imaging region 66 is adapted for projecting the (corresponding parts of) the primary field of view.

In the embodiment illustrated in FIG. 7, therefore, partial overlaps are applied at the axial edges (at the top and bottom edges of the useful field of view 60 shown in FIG. 7). The inconsistency of these partial overlaps can be resolved by moving the imaging device along a helical trajectory. Resolving the inconsistency of overlapping projections by moving the device along a helical trajectory is disclosed (to a case of a largely different application) in the above mentioned study by J. Lin, On Artifact-Free Projection Overlaps in Multi-Pinhole Tomographic Imaging, IEEE Trans. Med. Img., vol. 32, no. 12, (2013).

An imaging region layout corresponding to a further embodiment is illustrated in FIG. 8. As with the above described ones, in this embodiment there are no imaging regions assigned at the truncated corners of a useful field of view 80, and it also holds true that third imaging regions 88 are arranged along the straight edge segments of the useful field of view 80. Also, first and second supplementary pinholes are included in this embodiment, too, with corresponding respective first and second supplementary imaging regions 84, 99 that overlap in overlap regions 98.

It is noted that the first supplementary imaging regions 84 can additionally be classified among the second imaging regions corresponding to the second pinholes because they overlap with the third imaging regions 88 (this is the criterion for a region to be classified as a second imaging region). Furthermore—in contrast to the embodiment shown in FIG. 7—in this embodiment no supplementary imaging region is disposed along the extension of the column formed by first imaging regions 82. As shown in FIG. 8, the second supplementary imaging regions 99 may protrude from the useful field of view 80 to a small extent, but this essentially bears no significance as substantially no information is lost.

In an embodiment, furthermore, a column formed by the one or more first pinholes and/or a column formed by the one or more second pinholes and/or a column formed by the one or more third pinholes are shifted with respect to one another in a direction parallel with the field of view axis. The one shown in FIG. 8 is such an embodiment. In FIG. 8 there is shown that the columns of second imaging regions 84, 86 are shifted relative to the column of the first imaging regions 82 in a direction parallel with the field of view axis. Because in this embodiment there are no supplementary imaging regions in the extensions of the first imaging regions 82, but rather these places are taken by further first imaging regions 82, this shifting does not result in that there are arranged more second imaging regions 84, 86 than first imaging regions 82 (since from the aspect of imaging the central field of view the most important information is recorded in the first imaging regions 82, it is preferable if their number is the largest).

In addition to that, pinhole shifts corresponding to the shifted imaging regions result in that one more third imaging region 88 can be arranged in the useful field of view 80 than there are second imaging regions 86 non-overlapping with the second imaging regions 99 arranged therein (considering a column of the second imaging regions 86, the number of the latter is two). It is noted that with a useful field of view without corner truncations (e.g. with a photodetector matrix arranged in a square grid) the supplementary imaging regions 98 or 99 may extend as far as the vertical edges of the detector (as shown in the figure). In this case the individual imaging regions may have different sizes.

According to this arrangement, due to the axial shift in this embodiment more pinholes can be arranged on the collimator element (compared to the embodiment of FIG. 7), which significantly improves the sensitivity of the collimator element. In this embodiment, five first pinholes, four second pinholes in each second pinhole column, and three third pinholes in each third pinhole column are arranged on the collimator element (in contrast to that, in the case of the embodiment according to FIG. 7 these numbers are—also for other reasons—two, two, and two). By shifting the columns of pinholes with respect to one another (and thus by arranging the imaging regions appropriately) sensitivity can be increased significantly.

The detector surface segmentation arrangements shown in FIGS. 5-8 have the further advantage that the first imaging regions are situated in the middle of the useful field of view of the detector, where the detector has the most favourable intrinsic resolution, while the region being of lower interest with respect to the imaging quality, i.e. the region outside the CFOV but inside the primary FOV is projected on the third imaging regions 46, 58, 72 and 88 of the detector, which regions have significantly worse intrinsic resolution. Therefore, with such an arrangement higher-resolution images can be recorded of the regions of higher interest.

In the embodiments of the invention illustrated in FIGS. 5-8 the collimator element comprises second pinholes and third pinholes arranged symmetrically with respect to the one or more first pinholes on both sides of the one or more first pinholes. In the above embodiments therefore the columns of second and third pinholes are arranged symmetrically with respect to the column of first pinholes, i.e. in the collimator element the pinhole layout is symmetrical to the centreline of the collimator element.

If the photodetector elements, e.g. PMT-s—arranged on the side of the scintillation crystal lying opposite the incidence surface—are arranged in the detector in a hexagonal grid, the edge of the detector's useful field of view has a wavy shape corresponding to the structure of the PMT grid, which waves are conventionally cut off along the dashed line shown in the above referenced figures applying a mechanical shading element or electric iris.

It is however also possible to arrange the imaging regions along the transaxial edges (that is, the edges substantially parallel with the field of view axis) in such a manner (i.e. not regularly, as shown in FIGS. 5-8) that the useful field of view of the detector is utilized more efficiently. An example of that is shown in FIG. 9. In this case the individual imaging regions may have different sizes. Imaging regions with different sizes can also be applied in other embodiments.

In the embodiment of FIG. 9, therefore, the collimator element has a plurality of third pinholes, and the arrangement of the third imaging regions corresponding to the plurality of third pinholes follows a wavy shape of the edge of a useful field of view 100 of the detector along at least a part of the edge, preferably along that sides of the useful field of view of the detector which are parallel with the field of view axis (and not along the side perpendicular thereto).

In the embodiment according to FIG. 9 four first imaging regions 102 are arranged in the middle of the useful field of view 100, in a column parallel with the field of view axis; these regions image the central field of view in a non-overlapping manner. On each side of the column of the first imaging regions 102, a respective column of second imaging regions 106 and 109 is arranged. The imaging regions 106 and 109 have slightly different shape (and surface area) in order to conform to the shape of the useful field of view 100 (i.e. such that the appropriate overlaps with the third imaging regions can be formed while providing the largest possible size for the imaging regions).

According to FIG. 9 third imaging regions 104, 110 and 118 are arranged along one wavy edge, and third imaging regions 122, 123 and 119 along the other wavy edge of the useful field of view 100 following the shape of the given edge (i.e. extending into the recesses (as seen from inside) of the wavy edge (side)). Naturally, pinholes are also arranged corresponding to the imaging regions.

The third imaging region 104 overlaps with the second imaging region 106 in an overlap region 108. The third pinhole corresponding to the third imaging region 104 is preferably situated closer to the edge of the collimator element than the second pinhole corresponding to the second imaging region 106.

The third imaging region 110 also extends into a wave of the useful field of view 100, and also overlaps with two second imaging regions 106 and one second imaging region 109. The overlap with the upper second imaging region 106 is situated in an overlap region 112, and with the second imaging region 109 in an overlap region 114, and with the bottom second imaging region 106 in an almost negligibly small overlap region 116. On the other side of the first imaging regions 102 there are situated overlaps with different shapes between the third imaging regions 122, 123, 119 and the second imaging regions 106, 109, and the third imaging regions 119 and 122 are wider than the third imaging regions 108 and 118 (providing for a better utilization of the useful field of view 100). The overlap between the third imaging region 123 and the second imaging regions 106 and 109 is smaller than the overlap regions 112 and 114 situated on the other side, the third overlap region 123 being in overlap with only two second imaging regions (in contrast to the third imaging region 110). The third imaging regions 104, 110, 118, 119, 122, 123 extend out from the useful field of view 100 at certain locations but—since they are adapted for imaging the primary field of view—this does not have a significant effect.

Partially overlapping imaging region layouts that optimally fill the useful field of view of the detector may have a different number of first, second, and third imaging regions and supplementary imaging regions than what is presented in FIGS. 5-9.

Further opportunities offer themselves if the layout of the imaging regions (detector segments) is determined taking into account the local changes (fluctuations) of the intrinsic resolution of the detector. In FIG. 10 a corresponding segmentation of the useful field of view of the detector is presented according to an embodiment of the invention. In FIG. 10 the grayscale image shows the fluctuations of the local, intrinsic resolution of the detector (the shades essentially illustrate the local resolution at a given location).

In this embodiment a plurality of first imaging regions 132, a plurality of second imaging regions 133 and a plurality of third imaging regions 134 are centred on a central point of a region situated between adjacent photomultiplier constituting a triangle. where the FWHM (full width at half maximum) of the intrinsic resolution (the width of the point response function at the given location) is low (i.e. the resolution is better; these are the darker regions in the grayscale image).

With photomultipliers arranged in a hexagonal grid the poorest resolution (the highest FWHM) is obtained at the spots of the incidence surface of the detector that are situated above the respective centres of the photomultipliers. At these spots the incidence location calculated from the photodetector signals has relatively high uncertainty. Poor-resolution spots are surrounded by white areas also representing relatively poorer resolutions. The edges of these areas are grey, i.e. the resolution improves going further from these spots. The best local resolution is found at the centre of the triplets formed by adjacent photomultipliers. In FIG. 10 these spots and the surrounding areas are indicated by black patches. A similar solution can be conceived applying photodetectors arranged in a rectangular grid.

In certain embodiments of the invention, therefore, the detector is implemented by means of photodetectors, preferably photomultipliers, arranged in a hexagonal grid or in a rectangular grid. In such embodiments, preferably at least a part of the one or more first imaging regions, one or more second imaging regions and one or more third imaging regions are centred, in case of a hexagonal grid, on a central point of a region situated between the centres of three adjacent photodetectors constituting a triangle, or in case of a rectangular grid, on a central point of a region situated between the centres of four photodetectors constituting a rectangle.

As shown in FIG. 10, the first imaging regions 132 are arranged such that they are centred as much as possible on the black patches (blobs), i.e. on the highest-resolution areas surrounded by the photomultiplier triplets. The poor-resolution areas fall to the very thin strips between the imaging regions 132 (the width of these strips is reduced to the minimum possible in all embodiments, while of course avoiding an overlap with the imaging regions 132) or to the edges of each imaging regions 132, and thus images can be recorded with very favourable resolution over the major part of the imaging regions 132.

The second imaging regions 133 are also basically intended to be centred on the black patches; these regions are centred on the black patches to an extent that is similar to the first imaging regions 132. The third imaging regions 134 are situated at the left and right side of the useful field of view 130 as shown in the figure. These regions overlap (at overlap regions 136) with second imaging regions 133, some of them with more than one second imaging region, since in this embodiment the column of third imaging regions 134 (and thus also the third pinholes providing the imaging) is shifted with respect to the respective columns of the first and second imaging regions 132, 133 (and thus also with respect to the second and third pinholes) in a direction parallel with the field of view axis.

In the useful field of view 130 there are also arranged such imaging regions 135 that overlap with the lateralmost third imaging region 134, and are similarly focussed on the primary field of view. Furthermore, there are arranged such imaging regions 137 that are focussed on the primary field of view but do not overlap with any other imaging regions. The imaging regions 134 and also the imaging regions 135 and 137 are more or less centred on the black patches, but centring cannot be performed completely in all of the cases. With this detector segmentation, therefore, certain overlap regions (like the overlap region 136) lie in lighter, i.e. lower-resolution, areas.

Figure 11:
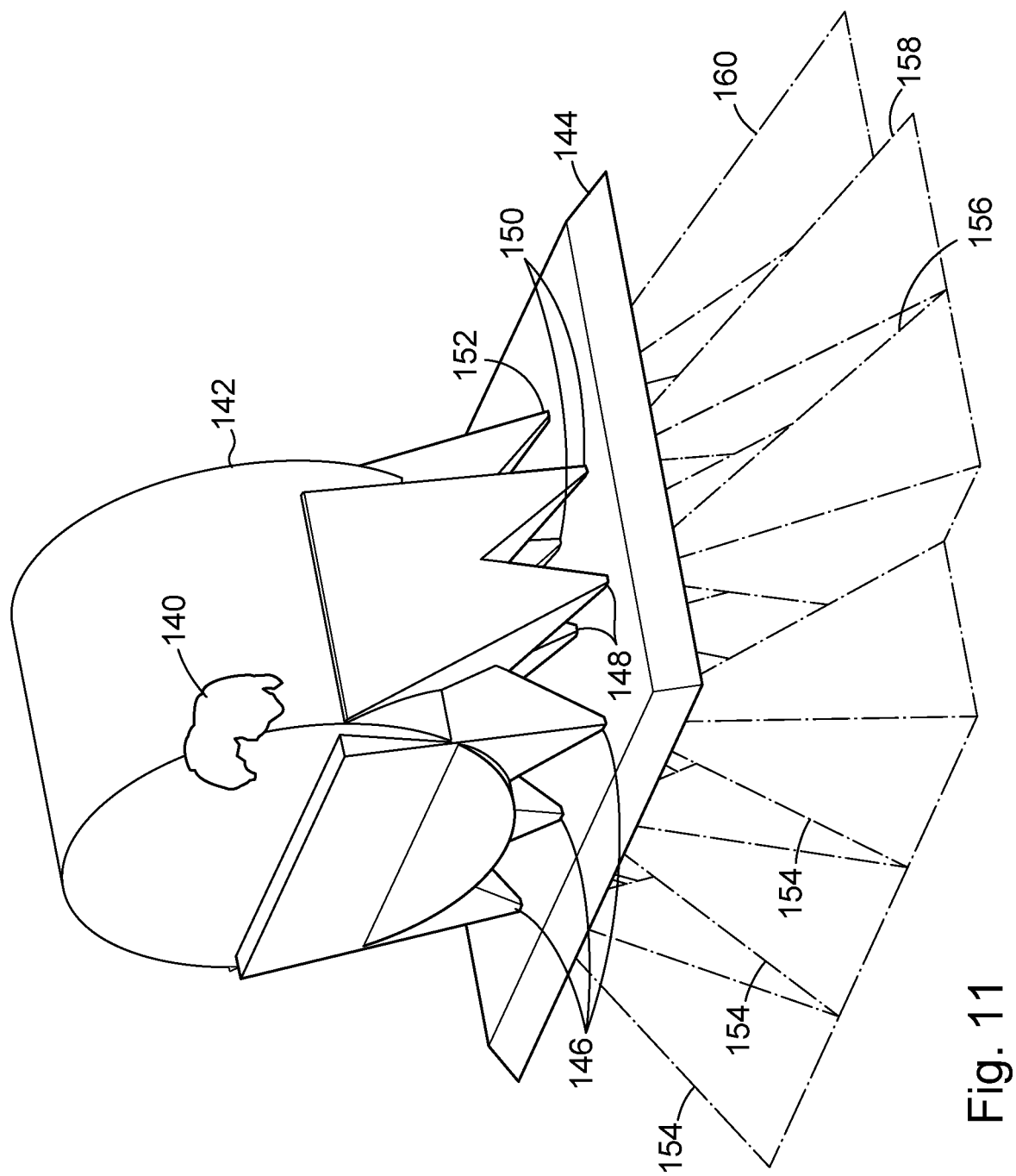
FIG. 11 is a schematic spatial drawing illustrating the imaging in an imaging device according to an embodiment of the invention.
Figure 12:
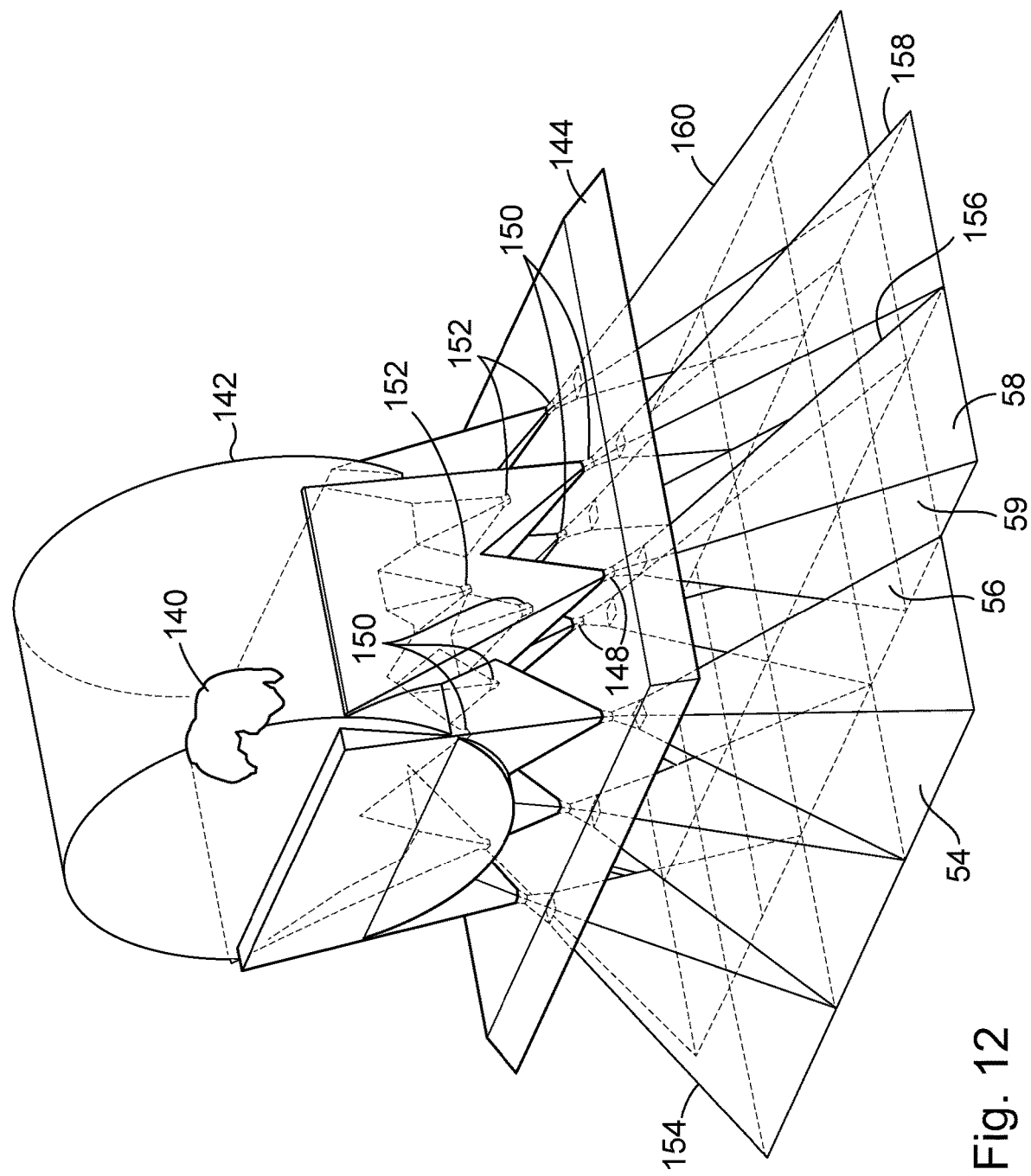
FIG. 12 is a further schematic spatial drawing illustrating the imaging according to FIG. 11.
Figure 13:
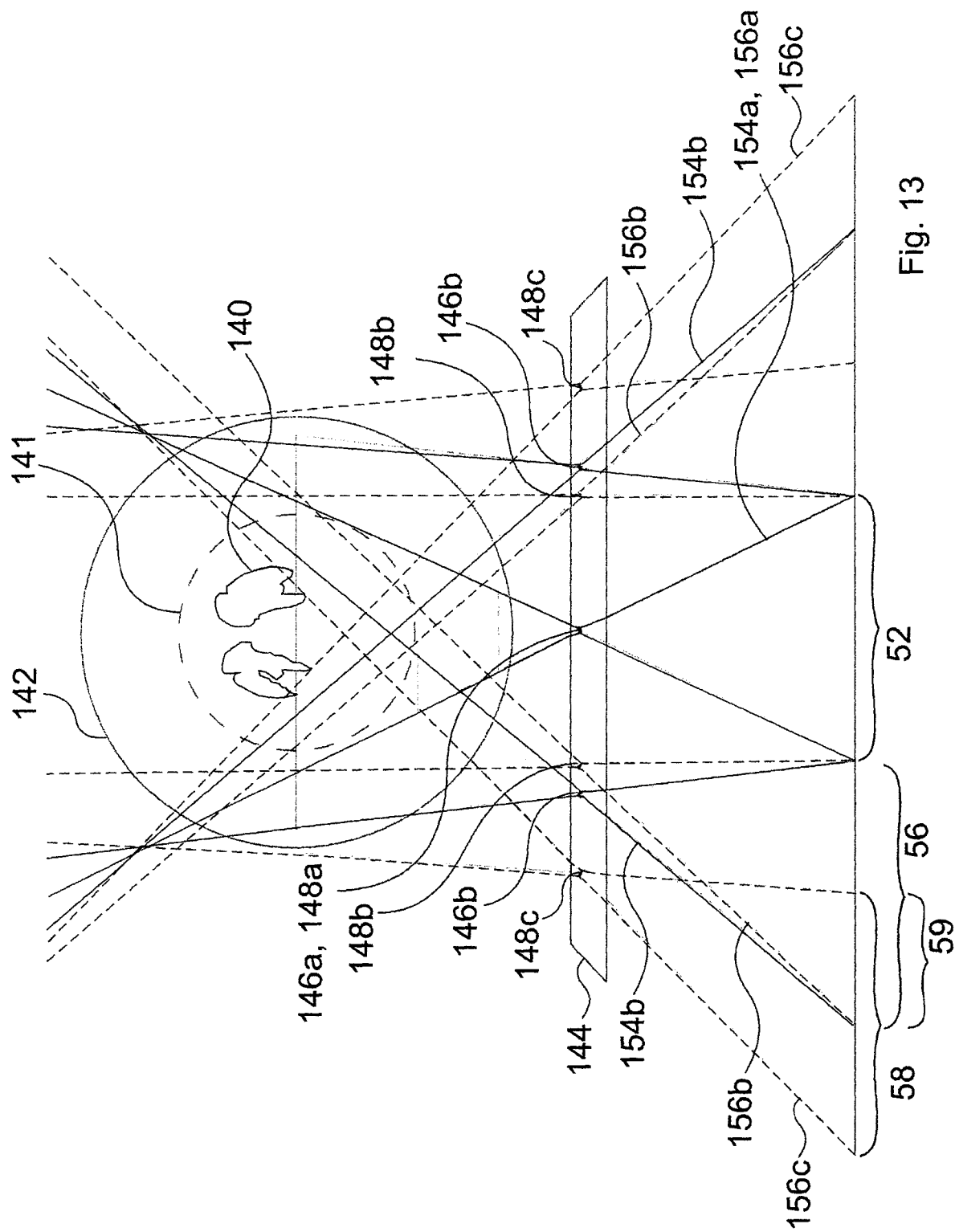
FIG. 13 is a drawing illustrating the imaging of FIG. 11 in front view.

An embodiment of the imaging device according to the invention is shown in FIGS. 11-14 in spatial and sectional views. In FIG. 11 a collimator element 144 of this embodiment is shown, and an object 140 to be examined, situated in a primary field of view 142. The object 140 falls into the central field of view 141 situated inside the primary field of view 142 and shown also in sectional views in FIGS. 13, 14. The central field of view 141 is a cylindrical region coaxial with the primary field of view 142, of which the peripheral cylindrical surface encompasses the object 140 to be examined, as shown in FIGS. 13 and 14.

The exact dimensions of the organ situated in the CFOV vary from individual to individual (both for humans and animals). In the imaging device the collimator element provided with pinholes and the corresponding detector determine the regions to be imaged on the side of the collimator element lying opposite the detector, i.e. the regions to which the individual projections are focussed or directed (the regions they cover). Accordingly, by specifying the projections (based on the configuration and shape of the pinholes) in the present invention, the location of the CFOV and the size of the primary FOV that the collimator element and the imaging device, also comprising a detector arranged at a fixed distance from the collimator element, are capable of imaging can be established. The CFOV region should be capable of accommodating reliably a larger-than-average organ to be examined.

Thereby, the exact path of the projection lines with respect to the CFOV thus established (whether they extend slightly outside or inside the boundary of the CFOV) is of secondary importance, what is most important is that the projections—particularly the non-overlapping ones—substantially image the CFOV. This substantially imaging holds true even in the case where the projection lines extend slightly inside the boundaries of the CFOV in the view under investigation. The organ to be examined falls into the projection with a high chance even in this case (since the CFOV is typically dimensioned to include a larger-than-average organ). Because during the recording process the imaging device is preferably rotated around the spatial region to be examined, or there are multiple imaging devices arranged around the spatial region to be examined, the small left-out region can be compensated for by a recording taken from another angle (the left-out region can appear therein).

The same are valid for imaging the primary FOV. According to the invention, the pinholes of the collimator element preferably image collectively substantially the entire primary FOV (especially the region thereof situated outside the CFOV, because the CFOV is imaged by the pinholes targeted at it on their own). In some embodiments (the embodiments shown in FIGS. 7-8) supplementary pinholes may be included in order to contribute to achieving as high an imaging ratio as possible.

Providing an imaging of the entire FOV from a given direction is not necessarily required in the case where the imaging device is rotated or there are more than one imaging devices arranged around the central and primary fields of view, and thereby a sufficient number of measurements are performed from other directions of non-imaged portions of the primary FOV in order that the CFOV can be reconstructed in a distortion-free and accurate manner. Similarly, it is also possible to record images with the imaging device from different angles and at different image-to-axis distances, typically taking into account the contours of the body to be examined. This also provides recordings from other directions.

The collimator element 144 shown in FIGS. 11-14 comprises sixteen pinholes. The illustrated sixteen-pinhole collimator element 144 provides the projection scheme onto the detector that is illustrated in FIG. 6, as it can also be observed in FIG. 12 (i.e. what has been set forth in relation to FIG. 6 also applies to the embodiments illustrated in FIGS. 11-14). As shown in FIG. 11, the pinholes form four rows in a direction perpendicular to the axis of the primary field of view 142 (the field of view axis, this direction is termed the transaxial direction), with three pinholes being arranged in the first and last row, and five pinholes being situated in the two middle rows.

In FIG. 11 each projection is illustrated by a pair of non-transparent pyramids meeting at their apexes at the corresponding pinhole. As shown in FIG. 11, the projections 154 of the first row are imaged on the detector in a non-overlapping manner. In the case shown in FIG. 11 the incidence surface of the detector lies in the plane where the pyramidal projections meet under the collimator element 144. In accordance with the invention, the lateralmost pairs of the projections 156 and 158 of the two middle rows provide overlapping imaging. The projections of the last row 160 provide non-overlapping imaging onto the detector.

According to FIG. 11 (and identically in FIG. 12) pinholes 146 are arranged in the first row, pinholes 148 in the second row, pinholes 150 in the third row, and pinholes 152 in the last row. The respective corresponding projections 148, 156, 158 and 160 pass through these pinholes 146, 148, 150 and 152.

In FIG. 12 only the outlines of the projections 154, 156, 158 and 160 (the edges of the pyramids) are shown, this is the reason why the imaging regions 52, 54, 56, 58 described above in relation to FIG. 6 are also shown in the figure. Thanks to the outline view, it is also shown which imaging regions 52, 54, 56, 58 correspond to which pinholes 146, 148, 150, 152. In addition to that, in FIG. 12 the outlines (the shape) of the pinholes 146, 148, 150 and 152 are also shown in accordance to the applied view.

As shown in FIG. 12, of the pinholes 146 of the first pinhole row (as seen in the axial direction) the middle one provides a projection on the imaging region 52, while the two lateral ones on the imaging regions 54. These projections are non-overlapping, with the imaging regions 52 and 54 being arranged on the detector surface tightly adjacently (in FIG. 6—and in the other similar figures—gaps are shown between the imaging regions only for the sake of a clearer observability, in reality the imaging regions are arranged as closely packed as possible). The pinholes 152 of the row lying last in the axial direction have a projection scheme analogous to that. Because the projections 154 are non-overlapping, the lateral pinholes 146 are essentially first pinholes as well because their projections do not overlap with the projections of any other pinhole, and are focussed to (provide an imaging of) the central field of view.

Of the pinholes 148 of the second row in the axial direction the middle one provides an imaging on the imaging region 52 situated below it, with the imaging region 52 being shifted in the axial direction (i.e. in a direction parallel with the field of view axis) relative to the imaging region 52 covered by the projection 154 provided by the first row. The two lateral ones of the pinholes 148 in the second row provide projection on the imaging regions 56 and 58 overlapping with each other. The overlap region 59 is also shown in FIG. 12. The pinholes situated at the other end of the row formed by the pinholes 148 provide an imaging in a manner analogous to these lateral pinholes (in an overlapping manner), and the third pinhole row comprising pinholes 150 provides an imaging in a manner analogous to the second row.

In FIG. 13 the collimator element 144 and the corresponding projections are shown in front view (in transaxial view). For the sake of clarity, in FIG. 13 the projections provided by the pinholes 146 situated in the first row in the axial direction (one pinhole 146a and two pinholes 146b) are shown in solid lines, while the projections provided by the pinholes 148 situated in the second row (one pinhole 148a and two-two pinholes 148b and 148c) are shown in dashed lines The pinholes 150 and 152 of the third and fourth row are obstructed from view due to a configuration identical to the pinholes 148 and 146. As it can be clearly seen also in FIG. 13, the pinholes 146 provide a non-overlapping imaging on the incidence surface of the detector that delimits the projections from below (the projections arrive at and overlap on the surface of the detector).

As with FIGS. 1-4, in FIG. 13 the imaging is shown in a transaxial view (perpendicular to the field of view axis), and therefore the projections provided by the pinholes can be observed in a transaxial view. FIG. 13 shows that in the transaxial view (i.e. when this view is considered) the central field of view 141 is imaged completely by the middle pinhole 146a of the first row, with the lines of the corresponding projection 154a passing along the central field of view 141, outside its boundary lines. The lateral pinholes 146b of the first row do not project the central field of view 141 completely, but in the illustrated view they image (project) the object 140 completely. They also provide a projection of a respective major portion of the primary field of view 142, and thereby in the illustrated transaxial view an imaging of the primary field of view 142 is substantially provided collectively by the pinhole 146a and the two pinholes 146b. In the case where the imaging device is applied for taking multiple images from different views by rotating the collimator element-detector assembly around the object 140 (i.e. about the centre of the circle representing the central field of view 141 in the illustrated view), a complete collective imaging can be provided of the primary field of view 142 from the different views by the pinholes 146a and 146b, and also of the central field of view 141 by for instance the pinholes 146b.

The pinholes 148 in the row situated second in the axial direction (the first pinhole 148a lying in the middle, and a respective pair of second and third pinholes 148b, 148c situated around it) on the collimator element 144 are also shown in FIG. 13. The projections 156a, 156b and 156c (collectively referred to as the projections 156) that correspond, respectively, to the pinholes 148a, 148b and 148c are shown in dashed lines in the figure. In the figure the pinhole 148a is obstructed from view by the pinhole 146a (the two pinholes coincide in this view), and therefore the projection 156a cannot be seen either (it is also obstructed from view) in the figure. Accordingly, an imaging of the entire central field of view 141 is provided by the pinhole 148a in the same way (i.e. considering the transaxial view) as by the pinhole 146a.

The second pinhole 148b and the third pinhole 148c provide an overlapping projection on the detector (with the imaging regions 52, 54 and 58 corresponding to the pinholes 148a, 148b and 148c being shown also in FIG. 13). The projection 156b of the pinhole 148b does not provide a complete imaging of the central field of view 141 because in the illustrated view one of the boundaries of the projection 148b goes across the central field of view 141 (at an outer part thereof). The other edge of the projection 156b passes outside the boundary of the central field of view 141. The boundaries of the projections 156b extend so close to the boundary of the central field of view 141 that the fact that one of them passes slightly inside the boundary of the central field of view 141 and the other slightly outside it has no practical significance. The projection 156b—like the projection 156a—is focussed on the central field of view 141 because the boundaries of the projection extend very close to the boundaries of the central field of view 141. It is shown also in FIG. 13 that the object 140 situated inside the central field of view 141 is projected by the pinholes 148b.

In FIG. 13 the projection 156c provided by the third pinholes 148 is also shown. The third pinholes 148c are situated at the edges of the collimator element 144. These third pinholes 148c are primarily directed at the primary field of view 142 (the projection 156c corresponding to the pinhole 148c is focussed on the primary field of view 142 because at least one of the boundaries of the projection 156c extends near the boundary of the primary field of view 142). One of the edges (boundaries) of the projections 156c extends right along the primary field of view 142 but outside the primary field of view 142, while the other boundary thereof goes across the primary field of view. The pinholes 148c provide an imaging of a major part of the primary field of view 142, and also an imaging of the object 140 situated in the central field of view 141.

The pinholes 148 are adjusted such that they can optimally provide an imaging of a larger-than-average organ. For imaging a different organ a collimator element specifically adjusted to match it can also be produced according to the invention by appropriately configuring the pinholes, bearing in mind the above described imaging principles (providing first, second and third type pinholes) and defining a central field of view encompassing the organ to be examined.

In FIG. 14 the projections are illustrated in a side view, i.e. in such a way that a field of view axis 15 shown in the figure lies in the plane of the drawing. The collimator element 144 and the pinholes 146, 148, 150 and 152 are shown in side view. The pinholes 146 and 152 are all situated in a single row (and thus the pinholes situated further back are obstructed from view by the front pinholes 146 and 152). However, the pinholes 148 and 150 are not completely located in the same row, certain pinhole(s) being shifted horizontally (i.e. to the side in the figure). Since the amount of this shift is very small, the pinholes 148 and 150 can be regarded as being situated in the same row (in the view according to FIG. 14 all projections corresponding to the pinholes 148 are essentially identical, which also holds true for the pinholes 150). As shown in FIG. 14, in the direction parallel with the field of view axis 15 the central field of view 141 is shorter than the primary field of view 142.

As shown in FIG. 14, in this view one of the boundaries of the projection 154 lies near the boundary of the primary field of view 142, the other boundary going across both the primary field of view 142 and the central field of view 141 (but the object 140 is imaged also by the projection 154). An imaging of the central field of view 141 is essentially provided by the projections 156, the projections also providing an imaging of a major part of the primary field of view 142 (one of their boundaries extending near the boundary of the central field of view 141). The same holds true for the projections 158. These provide an imaging of the central field of view 141 and of the major part of the primary field of view 142 at a slightly steeper angle compared to the projections 156.

The primary field of view 142 is situated essentially above the three rows of pinholes on the left of the figure (i.e. above the rows of pinholes 146, 148 and 150). This may e.g. be necessitated by placement constraints put on the collimator element and the detector by the requirement to place them in such a way relative to the volume to be examined—the central field of view 141 and the primary field of view 142—that they correspond to the geometry of the human body, Because of this, the projections 160 already image a portion of the central field of view 141 (the object 140 being situated in the imaged portion) and a further portion of the primary field of view 142 in a steeply inclined manner. Of course, however, the projection asymmetry shown in FIG. 14 is not a necessary feature, as the specific geometry of the organ or bodily surfaces to be imaged (e.g. the position of shoulder and arms) are always taken into account for designing the imaging.

In the axial direction of FIG. 14 imaging of an overwhelming the primary field of view 142 is provided by the projections 154, 156, 158 and 160.

In the above, a preferred embodiment designed for human brain investigations specific to Parkinson's disease is shown. Of course, in an analogous manner the herein described features can also be applied in a variety of other human diagnostic or pre-clinical devices (i.e. devices capable of performing in vivo scans of pets) adhering to the above presented design principles (the inclusion of first, second and third pinholes, the overlap between the projections provided by the second and third pinholes). By way of example, such devices can be applied for cardiology and renal scans.

The MP collimator element according to the invention illustrated in FIGS. 11-14 has been developed for a SPECT/CT apparatus (and apparatus comprising both a SPECT and a CT device). In accordance with the above, this collimator element allows specifically for brain scans related to Parkinson's disease. As it was detailed above, the imaging system was designed based on the imaging principle illustrated among others in FIG. 4, the useful field of view of the detector being segmented according to FIG. 6 such that according to the above the detector had a partially overlapping imaging.

A total of sixteen pinholes has been arranged on the collimator element 144, of which twelve is adapted for substantially completely projecting the CFOV and at the same time for resolving the inconsistency introduced by the overlapping projections provided by the four lateral pinholes directed at the FOV. At the same time the four pinholes providing projections on the lateral part of the detector allowed for gaining a sufficient amount of information on the activity situated outside the CFOV but inside the primary FOV. The projection is illustrated in a transaxial view in FIG. 13, in axonometric view in FIGS. 11-12, and in a side view in FIG. 14. The object 140 adapted to fit inside the CFOV situated in the primary FOV corresponds to putamen and caudate nuclei (striatum). The detector surface has a regular square-grid segmentation.

The imaging characteristics of the applied imaging has been calculated utilizing a self-developed Monte-Carlo based 3D reconstruction software (Tera-Tomo 3D SPECT) which takes into account the accurate gamma absorption and gamma scattering values of the inserts (blocks) carrying the pinholes of the collimator element and of the detector. The efficiency of the imaging is examined based on the accuracy calculated for the putamen and caudate regions (the ratio of the signal of the initial phantom averaged on the given region and the reconstructed image signal averaged on the same region, which has an optimum value of 1 if the initial phantom can be fully obtained from the reconstructed values) and on the CNR value.

For the calculation of accuracy and the CNR the change of the measured values and the contrast of the examined target regions has been examined compared to a reference region containing white matter (WM). For the reconstruction the OSEM algorithm (ordered-subset expectation maximization) has been applied.

In FIGS. 15-18 there is shown how these imaging characteristics (accuracy and CNR) change as a function of the number of iterations. The system used as a reference is a conventional MP collimator imaging system designed for imaging a human brain; imaging of this system is shown in FIGS. 15-18 with dashed lines. In the reference MP imaging the useful field of view of the detector (which is 540*400 mm$^2$) is divided into 12 parts, namely into 4*3 equal parts (transaxially: 4, axially: 3); each of the pinholes projects to one of these areas without overlap; the diameter of the pinholes is 4 mm. This arrangement is equivalent to the conventional MP imaging schematically illustrated in FIG. 1. On the other hand, the solid lines of FIGS. 15-18 illustrate the good quality imaging of the simulated results obtained with the embodiment of the invention illustrated in FIGS. 11-14. For the simulation a mathematical phantom of the brain and the Tera-Tomo 3D reconstruction code were applied, accurately modelling the response (gamma penetration and scatter) of the different collimators.

Figure 15:
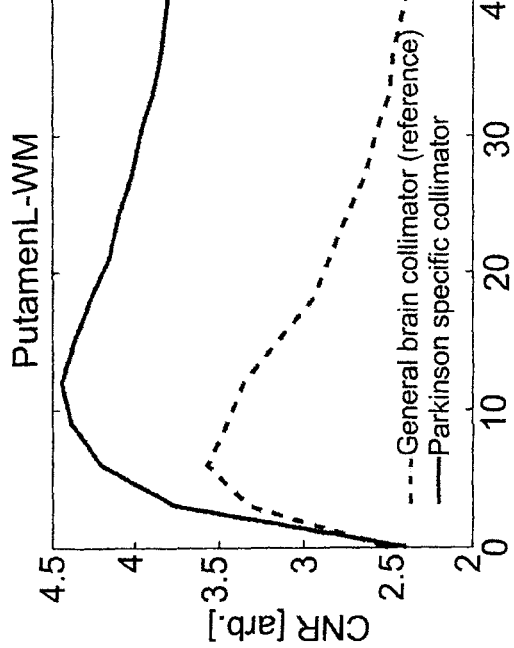
FIGS. 15 and 16 are diagrams showing the CNR as a function of the number of iterations.
Figure 16:
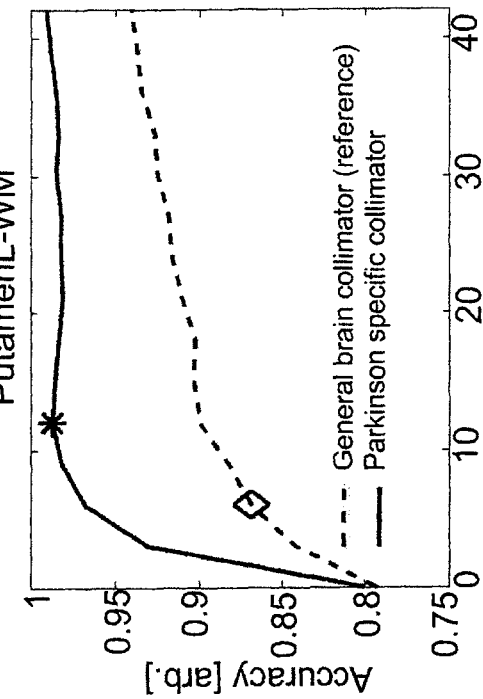
Figure 17:
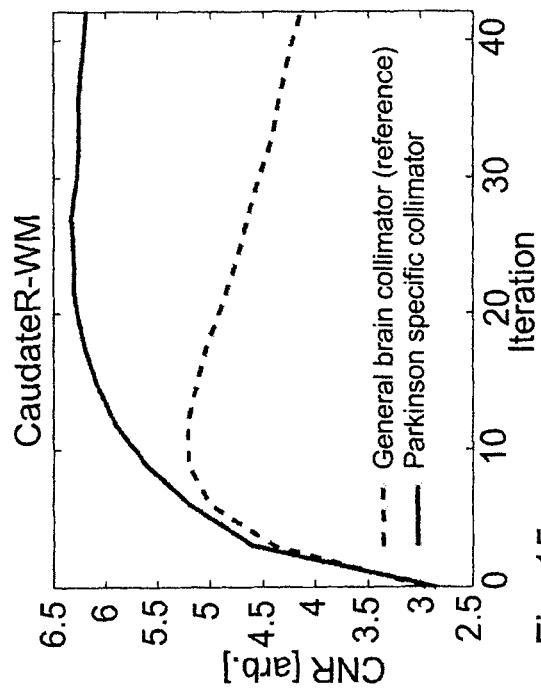
FIGS. 17 and 18 are diagrams showing accuracy as a function of the number of iterations.
Figure 18:
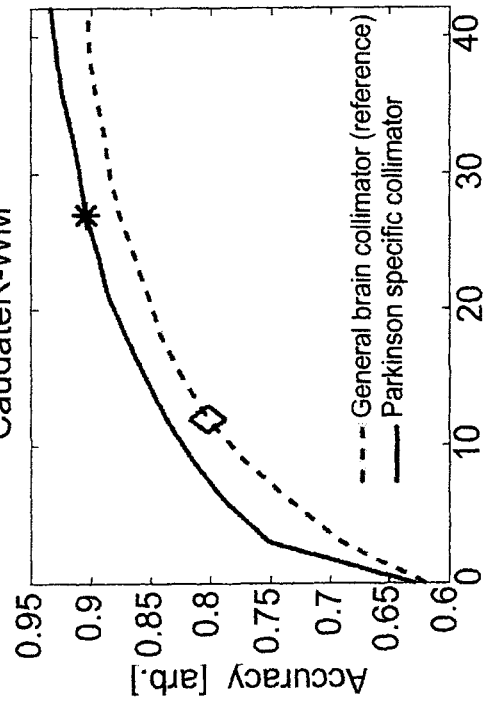

It can be seen that significantly higher CNR values can be achieved applying the Parkinson's-specific solution related to the present invention (for the caudate region, see FIG. 15, and also for the putamen region, see FIG. 16; in the diagrams it is shown whether the results are for the putamen or caudate nuclei of the left (L) or right (R) hemisphere, with the abbreviation WM being included because noise is examined in a brain segment of white matter) compared to the conventional solution (the contrast has been improved while the background noise has dropped). For higher iteration numbers (above approximately 10) a particularly large difference can be observed between the results obtained with the two different imaging devices.

The accuracy calculated at the maximum CNR value (where the iteration can preferably be halted) is shown by an asterisk (*) and a diamond symbol (in FIG. 17 this point is located approximately at the 28th iteration for the caudate region, while for the putamen—in FIG. 18—already at approx. the 12th iteration) i.e. the imaging accuracy of the target regions has been improved significantly (has come nearer the ideal value of 1).

Figure 19:
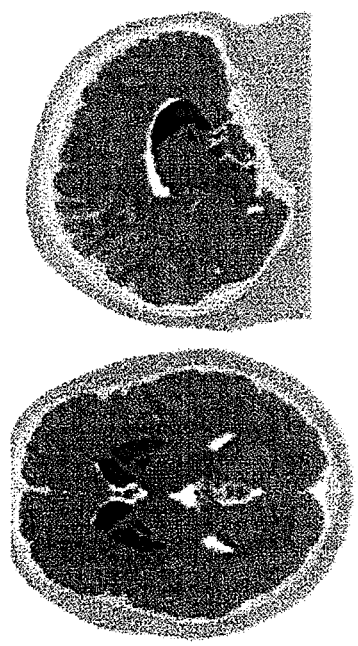
FIG. 19 illustrates the mathematical phantom of the brain.
Figure 21:
FIG. 21 shows a reconstruction obtained by reconstructing an imaging of the brain taken applying the imaging device according to the invention.
Figure 20:
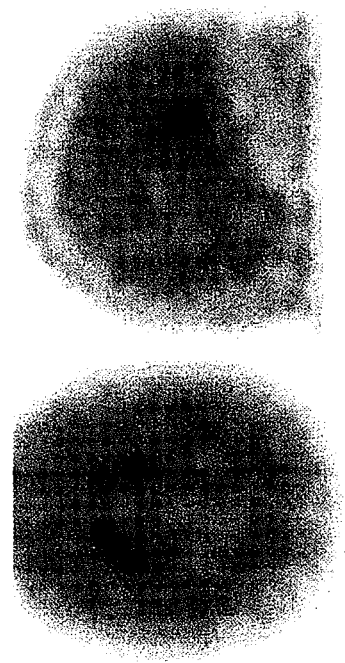
FIG. 20 shows a reconstruction of an imaging of the brain applying a generic brain collimator.

Having a look at the reconstructed transaxial sections of the brain phantom (the original mathematical phantom is shown in FIG. 19) imaged applying a conventional collimator element (see FIG. 20) and a collimator element according to the embodiment of the invention illustrated in FIGS. 11-14 (see FIG. 21), it can be observed that the Parkinson's-specific collimator element according to the invention provides a sharper imaging of the target regions (indicated by arrows, cf. the phantom shown in FIG. 19), while the noise content of the background is also significantly reduced.

In FIGS. 11-21 a preferred embodiment is illustrated that may form a part of a Parkinson's-specific imaging system. An exemplary implementation of such a system can be based on the AnyScan TRIO triple-head SPECT camera developed by the present applicant. This device can be reconfigured by applying a collimator element conforming to the principles of the invention (thereby producing an imaging device according to an embodiment of the invention).

An example may be implemented with the following dimensions. The AnyScan TRIO camera (detector) has a useful field of view (UFOV) of 540 mm*415 mm and an intrinsic resolution (FWHM) of 2.5 mm. The diameter of the FOV is 220 mm, its length is 180 mm, the diameter of the CFOV is approx. 120 mm and its length is also approx. 120 mm. In manner indicated in FIG. 6 the useful field of view was divided into 5*4 identical projections, and for the above described reasons the corner projections were omitted. The distance between the axis of rotation (field of view axis) of the exemplary imaging system and the detector (i.e. the plane of the NaI crystal proximate the detector) is 285 mm, while the distance between the focal plane of the pinholes and the axis is 140 mm. The thickness of the collimator element (aperture) comprising the pinholes is 18 mm (the focal plane is situated at a distance of 5 mm from the inlet side [shown at the top in the figure]). The pinholes have been provided in 3D-printed Tungsten inserts. The bores of the pinholes (their smallest cross section) have been a square (also according to FIG. 13 the bores are inclined in many cases), the diagonal of the squares having a length of 4.0 mm for the first and second type pinholes and 5.0 mm for the third type pinholes (4 pinholes).

As described above, the first type pinholes have been focussed directly on the CFOV, and these pinholes provide a complete and unambiguous imaging of the CFOV (comprising the putamen and caudate nuclei). For determining the position of the remaining pinholes—in addition to the principles set forth in this description—such an optimization method (a global optimum-finding technique termed "simulated annealing") has been applied that adjusted the focal points and directions of the pinholes such that the maximum values of the CNR curves shown in FIGS. 15-18 are as high as possible and that the highest possible accuracy is achieved at these maximums.

Some embodiments of the invention relate to a tomography apparatus, particularly a SPECT apparatus. The tomography apparatus according to the invention comprises an embodiment of the imaging device according to the invention. Naturally, the tomography apparatus comprises a region adapted for receiving a patient, around which region—and thus around the field of view axis—typically more than one imaging devices are arranged or rotated. The imaging device is mounted or moved inside the tomography apparatus by means of a positioning unit. The tomography apparatus typically also comprises data acquisition electronics and a computer for processing the collected data, a computer adapted for 3D image reconstruction, and a reconstruction software adapted for taking into account data acquisition, image corrections, and the model of the collimator unit. The computer can also be applied for running the reconstruction software adapted for performing the reconstruction based on the measured data.

In an embodiment of the tomography apparatus the imaging device is rotatable around the field of view axis in the tomography apparatus. The imaging device comprising a collimator element and a detector can therefore be applied for recording images of the object typically situated in the central field of view, i.e. according to the principles detailed above, of the central field of view and the primary field of view, from multiple directions. In other tomography apparatuses comprising rotatable imaging devices the tomography recordings are typically made such that the imaging device is halted at multiple discrete angular values, or recordings are made continuously during the rotation; and, provided that the rotation parameters are available, the orientation of the imaging device relative to the primary and central fields of view at the time a given scintillation (an event induced by a photon) has been recorded can be calculated.

In a further embodiment of the tomography apparatus according to the invention a plurality of imaging devices (in an example, three imaging devices) are arranged in respective positions rotated relative to one another about the field of view axis. In this configuration, due to the fixed position of the imaging devices the angle at which the activity distribution present primarily in the central field of view but possibly also in the primary field of view is seen in a given recording is known from the beginning.

The invention is, of course, not limited to the preferred embodiments described in details above, but further variants, modifications and developments are possible within the scope of protection determined by the claims.

The invention claimed is:
1. An imaging device comprising:
   a detector adapted to determine a point of incidence of a photon, and having an incidence surface,
   a collimator element adapted to project the photon onto the detector, the collimator element including:
      an inlet surface,
      an outlet surface facing the incidence surface of the detector, and
      a plurality of pinholes each connecting the inlet surface and the outlet surface, the plurality of pinholes including:
         a first pinhole focused on a central spatial region having a cylindrical shape and a first axis of symmetry, the first pinhole adapted to project the central spatial region onto a first imaging region on the incidence surface of the detector,
         a second pinhole focused on the central spatial region and shifted with respect to the first pinhole in a direction perpendicular to the first axis of symmetry, the second pinhole adapted to project the central spatial region onto a second imaging region on the incidence surface of the detector that does not overlap the first imaging region, and
         a third pinhole focused on a primary spatial region having a cylindrical shape larger than and encompassing the central spatial region and a second axis of symmetry coincident with the first axis of symmetry of the central spatial region, the third pinhole adapted to project the primary spatial region onto a third imaging region on the incidence surface of the detector that overlaps the second imaging region and does not overlap the first imaging region.
2. The imaging device according to claim 1, wherein each of the first pinhole, the second pinhole, and the third pinhole have a pyramidal configuration.
3. The imaging device according claim 1, wherein the detector includes photodetectors arranged in one of a hexagonal grid or a rectangular grid.
4. The imaging device according to claim 3, wherein at least a part of each of the first imaging region, the second imaging region, and the third imaging region is:
   in cases where the photodetectors are arranged in the hexagonal grid, centered on a central point of a region situated between the centers of three adjacent photodetectors constituting a triangle, and
   in cases where the photodetectors are arranged in the rectangular grid, centered on a central point of a region situated between the centers of four adjacent photodetectors constituting a rectangle.
5. The imaging device according to claim 3, wherein the third imaging region is one of a plurality of third imaging regions and the third pinhole is one of a plurality of third pinholes each configured to project the primary spatial region onto a different third imaging region on the incidence surface of the detector, and an arrangement of the plurality of third imaging regions follows a wavy shape of the edge of a useful field of view of the detector along at least a part of the edge.
6. The imaging device according claim 3, wherein the third imaging region is one of a plurality of third imaging regions and the third pinhole is one of a plurality of third pinholes each configured to project the primary spatial region onto a different third imaging region on the incidence surface of the detector, a useful field of view of the detector has a shape of a rectangle with cut corners, and the plurality of third imaging regions are arranged along a straight line segment extending between the cut corners.
7. The imaging device according to claim 1, wherein the second pinhole is one of a pair of second pinholes, the third pinhole is one of a pair of third pinholes, and each of the second pinholes and each of the third pinholes are arranged symmetrically with respect to and on opposite sides of the first pinhole.
8. The imaging device of claim 1, wherein:
   the first pinhole is one of a plurality of first pinholes arranged so that each first pinhole is shifted with respect to the other first pinholes in a direction parallel with the first axis of symmetry,
   the second pinhole is one of a plurality of second pinholes arranged so that each second pinhole is shifted with respect to the other second pinholes in a direction parallel with the first axis of symmetry, and
   the third pinhole is one of a plurality of third pinholes arranged so that each third pinhole is shifted with respect to the other third pinholes in a direction parallel with the first axis of symmetry.
9. The imaging device according to claim 8, wherein at least one of a column formed by the first pinholes, a column formed by the second pinholes, and a column formed by the third pinholes is shifted with respect to the other columns in the direction parallel with the first axis of symmetry.
10. The imaging device according to claim 8, wherein the collimator element further comprises:
    a first supplementary pinhole arranged in a position shifted with respect to the lateralmost of the first pinholes, the second pinholes, and the third pinholes in the direction parallel with the first axis of symmetry, the first supplementary pinhole being adapted to project the central spatial region on a first supplementary imaging region on the incidence surface of the detector, and
    a second supplementary pinhole arranged in a position shifted with respect to the first supplementary pinhole in the direction parallel with the first axis of symmetry and adapted to project the primary spatial region on a second supplementary imaging region overlapping with the first supplementary imaging region on the incidence surface of the detector.
11. The imaging device of claim 8, wherein:
    the first imaging region is one of a plurality of first imaging regions;
    the second imaging region is one of a plurality of imaging regions;
    the third imaging region is one of a plurality of third imaging regions;
    each of the first pinholes is adapted to project the central spatial region onto a different first imaging region on the incidence surface of the detector,
    each of the second pinholes is adapted to project the central spatial region onto a different second imaging region on the incidence surface of the detector, and none of the second imaging regions overlap any of the first imaging regions, and
    each of the third pinholes is adapted to project the primary spatial region onto a different third imaging region on the incidence surface of the detector that overlaps a different one of the second imaging regions and does not overlap any of the first imaging regions.

12. A tomography apparatus comprising the imaging device according to claim 1.

13. The tomography apparatus according to claim 12, wherein the imaging device is rotatable around the first axis of symmetry.

14. The tomography apparatus according to claim 12, wherein a plurality of imaging devices are arranged in respective positions rotated relative to one another about the first axis of symmetry.

* * * * *